(12) United States Patent
Yoshikawa et al.

(10) Patent No.: US 9,212,959 B2
(45) Date of Patent: Dec. 15, 2015

(54) SURFACE STRESS SENSOR

(75) Inventors: Genki Yoshikawa, Tsukuba (JP);
Heinrich Rohrer, Tsukuba (JP);
Terunobu Akiyama, Neuchatel (CH);
Vettiger Peter, Neuchatel (CH)

(73) Assignee: National Institute for Materials Science, Ibaraki (JP)

( * ) Notice: Subject to any disclaimer, the term of this patent is extended or adjusted under 35 U.S.C. 154(b) by 168 days.

(21) Appl. No.: 13/699,667

(22) PCT Filed: May 9, 2011

(86) PCT No.: PCT/JP2011/060673
§ 371 (c)(1),
(2), (4) Date: Feb. 14, 2013

(87) PCT Pub. No.: WO2011/148774
PCT Pub. Date: Dec. 1, 2011

(65) Prior Publication Data
US 2013/0133433 A1 May 30, 2013

(30) Foreign Application Priority Data

May 24, 2010 (JP) .................................. 2010-118859

(51) Int. Cl.
G01B 7/16 (2006.01)
G01L 1/18 (2006.01)
G01N 29/02 (2006.01)

(52) U.S. Cl.
CPC .............. *G01L 1/18* (2013.01); *G01N 29/022* (2013.01); *G01N 2291/02466* (2013.01)

(58) Field of Classification Search
CPC ..................................... G01B 7/16; G01L 1/18
USPC ................................................... 73/774, 105
See application file for complete search history.

(56) References Cited

U.S. PATENT DOCUMENTS

| | | | | |
|---|---|---|---|---|
| 3,304,787 A * | 2/1967 | Takewo Chiku et al. | .. | 73/514.33 |
| 3,500,451 A * | 3/1970 | Yando | ........................... | 310/330 |
| 4,614,245 A * | 9/1986 | Yamanaka | .............. | 177/210 FP |
| 4,849,730 A | 7/1989 | Izumi et al. | | |
| 5,239,870 A * | 8/1993 | Kaneko | ....................... | 73/514.33 |
| 6,211,540 B1 * | 4/2001 | Takahashi et al. | ............ | 257/252 |
| 6,311,557 B1 * | 11/2001 | Davis et al. | ................. | 73/514.31 |
| 6,479,920 B1 * | 11/2002 | Lal et al. | ....................... | 310/309 |
| 7,535,155 B2 * | 5/2009 | Ishikawa | ...................... | 310/339 |
| 7,560,070 B1 * | 7/2009 | Baller et al. | .................... | 422/50 |

FOREIGN PATENT DOCUMENTS

| | | |
|---|---|---|
| JP | 56-23316 | 5/1981 |
| JP | 63-12930 | 1/1988 |
| JP | 6-230023 | 8/1994 |

OTHER PUBLICATIONS

International Search Report issued Jul. 26, 2011 in corresponding International Application No. PCT/JP2011/060673.

* cited by examiner

*Primary Examiner* — Lisa Caputo
*Assistant Examiner* — Octavia Hollington
(74) *Attorney, Agent, or Firm* — Wenderoth, Lind & Ponack, L.L.P.

(57) ABSTRACT

Deflection of a free end of one plate-like member, that is caused by uniform stress, is transmitted to an other plate-like member by moving a free end of the other plate-like member. According to this configuration, the uniform stress applied to the one plate-like member is converted into stress induced by a point force in the other plate-like member, and then, the induced stress is concentrated on a fixed end side narrow portion in which a piezoresistor is provided. Thus, a novel structure for a piezoresistive surface stress sensor having high sensitivity to uniform stress applied to the surface of the sensor is provided.

10 Claims, 10 Drawing Sheets

SURFACE STRESS SENSOR

TECHNICAL FIELD

The present invention relates to a piezoresistive surface stress sensor (SSS) having a much higher sensitivity compared with a piezoresistive cantilever sensor in the related art.

BACKGROUND ART

A cantilever array sensor has attracted wide interest by having various advantages such as real-time and label-free detection characteristics (Non-Patent Document 1). Applications including an electric nose (Non-Patent Documents 2 and 3) and chemical and biological detection (Non-Patent Documents 4 to 9) that employ a cantilever array have been proposed. Most of this research employs optical reading using a laser reflected from a surface of a cantilever, which causes several important problems with respect to the actual application of this technique. First of all, a laser device and its peripheral devices for reading are expensive and are difficult to miniaturize. In addition, target molecules in an opaque liquid such as blood can not be detected by the optical reading technique because a signal is considerably attenuated and a refractive index is considerably changed, which is not suitable for use.

One of the most promising solutions for these problems is a piezoresistive cantilever array sensor (Non-Patent Document 10). In a cantilever sensor, a sample is adsorbed onto a receptor layer fabricated in advance on a surface of a cantilever to induce surface stress, which deflects the cantilever. Thus, by detecting the deflection, it is possible to detect the sample. FIG. 1 illustrates an example of a structure of a piezoresistive cantilever array sensor, which is a cross-sectional view of a part close to a fixed end of a cantilever. In this example, a piezoresistive member is built into a surface of the cantilever and is protected by a nitride film. Thus, the upward/downward deflection of the cantilever due to stress on the surface of the cantilever causes compression/elongation strain in the piezoresistive member, which changes the resistance of the piezoresistive member. Such a change of the piezoresistive member caused by the surface stress is detected by an electric circuit as schematically shown in FIG. 2. As shown in the figure, four sides, that is, the piezoresistive member of the measured cantilever shown in FIG. 1, a reference cantilever and two resistors form a bridge. Here, a change in resistance of one side, that is, the piezoresistive member in the measured cantilever can be detected, in a state where voltage is applied to a pair of corners of the bridge, on the basis of voltage of the other pair of opposing corners.

As understood from the above-mentioned operating principle, the piezoresistive cantilever array sensor does not need complex and bulky peripheral devices relating to optical reading. Further, the piezoresistive cantilever array sensor can be manufactured in the same process as a complementary metal-oxide semiconductor (CMOS), and is thus possible to be low cost due to mass production and integrated into existing semiconductor devices such as a mobile phone due to micro miniaturization. Further, this sensor is usable for detection in an arbitrary opaque liquid. Although the piezoresistive cantilever array sensor has these attractive advantages, this type of sensor is not yet sufficiently optimized.

In order to enhance sensitivity of the piezoresistive cantilever, various solutions have been proposed so far. Non-Patent Document 11 discloses a technique in which various factors such as art annealing time, a doping level and a measuring frequency are considered to obtain a signal-to-noise (S/N) ratio of about 10. It is shown that a multilayer cantilever using a residual stress in each layer has superior curvature and sensitivity (Non-Patent Document 12). Various shapes such as various positions of a patterned surface or a receptor layer are discussed to obtain an improvement of sensitivity of several tens of percent (Non-Patent Document 13). However, all this research is based on a normal cantilever shape having a free end, and has a basic problem of the piezoresistive cantilever, that is, a problem that sensitivity is low with respect to stress of the entire surface caused by a sample uniformly distributed without concentration.

A solution for optimizing the piezoresistive cantilever toward a detection application, that is, detection of surface stress caused by a sample is not the same as a solution for a normal atomic force microscope (AFM) or an optical reading cantilever. A sensor for the AFM is based on "a point force", that is, a force applied to a probe disposed at a free end of a scanning cantilever. On the other hand, a cantilever sensor is based on "surface stress" uniformly induced on an overall surface of a cantilever (Non-Patent Documents 14 and 15). Respective portions of the cantilever are equivalently deflected by the surface stress, and as a result, displacement is accumulated toward the free end. Thus, the displacement is at a maximum at the free end. In the optical reading system, a laser is typically reflected at a free end of a cantilever. Thus, the entire surface stress induced on the cantilever can be efficiently detected.

On the other hand, a signal of the piezoresistive cantilever does not depend on the displacement of the free end, but depends on the stress induced in a piezoresistor. In the case of the scanning cantilever, where the point force is applied to the free end, the stress is concentrated in the vicinity of a fixed end, but in the case of the cantilever sensor, only a part of the stress induced by the sample can be detected by the piezoresistor. It is because this stress uniformly spreads on the entire surface. Thus, in order to acquire larger stress in the piezoresistive part to achieve higher sensitivity, another optimal solution for the piezoresistive cantilever array sensor is necessary.

Non Patent Document 16 discloses a vertically layered cantilever structure for improvement in sensitivity. However, in this design, a double-layer structure is necessary, which causes difficulties in manufacturing.

PRIOR ART DOCUMENTS

Non-Patent Documents

NON-PATENT DOCUMENT 1: Lang, H. P., Nanomechanical Cantilever Array Sensors. In Springer Handbook of Nanotechnology, Bhushan, B., Ed. 2007; p 443.

NON-PATENT DOCUMENT 2: Lang, H. P.; Baller, M. K.; Berger, R.; Gerber, C.; Gimzewski, J. K.; Battiston, F. M.; Fornaro, P.; Ramseyer, J. P.; Meyer, E.; Guntherodt, H. J. Anal. Chim. Acta 1999, 393, 59.

NON-PATENT DOCUMENT 3: Baller, M. K; Lang, H. P.; Fritz, J.; Gerber, C.; Gimzewski, J. K.; Drechsler, U.; Rothuizen, H.; Despont, M.; Vettiger, P.; Battiston, F. M.; Ramseyer, J. P.; Fornaro, P.; Meyer, E.; Guntherodt, H. J. Ultramicroscopy 2000, 82, 1.

NON-PATENT DOCUMENT 4: Fritz, J.; Baller, M. K.; Lang, H. P.; Rothuizen, H.; Vettiger, P.; Meyer, E.; Guntherodt, H. J.; Gerber, C.; Gimzewski, J. K. Science 2000, 288, 316.

NON-PATENT DOCUMENT 5: McKendry, R.; Zhang, J. Y.; Arntz, Y.; Strunz, T.; Hegner, M.; Lang, H. P.; Baller, M. K.; Certa, U.; Meyer, E.; Guntherodt, H. J.; Gerber, C. Proc. Natl. Acad. Sci. U.S.A. 2002, 99, 9783.

NON-PATENT DOCUMENT 6 Arntz, Y.; Seelig, J. D.; Lang, H. P.; Zhang, J.; Hunziker, P.; Ramseyer, J. P.; Meyer, E.; Hegner, M.; Gerber, C. Nanotechnology 2003, 14, 86.

NON-PATENT DOCUMENT 7; Backmann, N.; Zahnd, C.; Huber, F.; Bietsch, A.; Pluckthun, A.; Lang, H. P.; Guntherodt, H. J.; Hegner, M.; Gerber, C. Proc. Natl. Acad. Sci. U.S.A. 2005, 102, 14587.

NON-PATENT DOCUMENT 8: Zhang, J.; Lang, H. P.; Huber, F.; Bietsch, A.; Grange, W.; Certa, U.; McKendry, R.; Guentherodt, H.-J.; Hegner, M.; Gerber, C. Nat. Nanotechnol. 2006, 1, 214

NON-PATENT DOCUMENT 9: Watari, M.; Galbraith, J.; Lang, H. P.; Sousa, M.; Hegner, M.; Gerber, C.; Horton, M. A.; McKendry, R. A. J. Am. Chem. Soc. 2007, 129, 601.

NON-PATENT DOCUMENT 10: Yoshikawa, G.; Lang, H.-P.; Akiyama, T.; Aeschimann, L.; Staufer, U.; Vettiger, P.; Aono, M.; Sakurai, T.; Gerber, C. Nanotechnology 2009, 20, 015501.

NON-PATENT DOCUMENT 11: Yu, X. M.; Thaysen, J.; Hansen, O; Boisen, A. J. Appl. Phys. 2002, 92, 6296.

NON-PATENT DOCUMENT 12: Choudhury, A.; Hesketh, P. J.; Thundat, T.; Hu, Z. Y. J. Micromech, Microeng. 2007, 17, 2065.

NON-PATENT DOCUMENT 13 Privorotskaya, N. L.; King, W. P. Microsyst Technol 2008, 15, 333.

NON-PATENT DOCUMENT 14: Rasmussen, P. A.; Hansen, 0.; Boisen, A. Appl. Phys. Lett. 2005, 86, 203502.

NON-PATENT DOCUMENT 15: Sader, J. E. J. Appl. Phys. 2001, 89, 2911.

NON-PATENT DOCUMENT 16: Yang, S. M.; Yin, T. I.; Chang, C. Sens. Actuators B 2007, 121, 545.

NON-PATENT DOCUMENT 17: Kanda, Y. IEEE Trans. Electron Devices 1982, 29, 64.

NON-PATENT DOCUMENT 18: Kanda, Y. Sens. Actuators A 1991, 28, 83.

NON-PATENT DOCUMENT 19: Pfann, W. G.; Thurston, R. N. J. Appl. Phys. 1961, 32, 2008.

NON-PATENT DOCUMENT 20: Stoney, G. G. Proc. R. Soc. London, Ser. A 1909, 82, 172.

NON-PATENT DOCUMENT 21: Aeschimann, L.; Meister, A.; Akiyama, T.; Chui, B. W.; Niedermann, P.; Heinzelmann, H.; De Rooij, N. F.; Staufer, U.; Vettiger, P. Microelectron. Eng. 2006, 83, 1698.

NON-PATENT DOCUMENT 22: Aeschimann, L.; Goericke, F.; Polesel-Maris, J.; Meister, A.; Akiyama, T.; Chui, B.; Staufer, U.; Pugin, R.; Heinzelmann, H.; Rooij, N. F. d.; King, W. P.; Vettiger, P. J. Phys. 2007, 61, 6.

NON-PATENT DOCUMENT 23: Binnig G, Quate C F and Gerber C 1986 Atomic Force Microscope Phys. Rev, Lett. 56 930-3)

NON-PATENT DOCUMENT 24: Drake B, Prater C B, Weisenhorn A L, Gould S A C, Albrecht T R, Quate C F, Cannell S, Hansma H G and Hansma P K 1989 Imaging Crystals, Polymers, and Processes in Water with the Atomic Force Microscope Science 243 1586-9)

NON-PATENT DOCUMENT 25: Rugar D, Mamin H J and Guethner P 1989 Improved Fiber-Optic Interferometer for Atomic Force Microscopy Appl. Phys. Lett. 55 2588-90

NON-PATENT DOCUMENT 26: Martin Y, Williams C C and Wickramasinghe H K 1987 Atomic Force Microscope Force Mapping and Profiling on a Sub 100-a Scale J. Appl. Phys. 61 4723-9

NON-PATENT DOCUMENT 27: Yoshikawa G, Lang H-P, Akiyama T, Aeschimann L, Staufer U, Vettiger P, Aono M, Sakurai T and Gerber C 2009 Sub-ppm detection of vapors using piezoresistive microcantilever array sensors Nanotechnology 20 015501

NON-PATENT DOCUMENT 28; Tortonese M, Barrett R C and Quate C F 1993 ATOMIC RESOLUTION WITH AN ATOMIC FORCE MICROSCOPE USING PIEZORESISTIVE DETECTION Appl. Phys. Left. 62 834-6

NON-PATENT DOCUMENT 29: Vettiger P, et al. 2002 The "millipede"—Nanotechnology entering data storage IEEE Trans. Nanotechnol. 1 39-55

SUMMARY OF THE INVENTION

Problems that the Invention is to Solve

It is an object of the present invention to provide a surface stress sensor having a novel and simple structure that provides high sensitivity compared with a piezoresistive cantilever array sensor in the related art.

Means for Solving the Problems

In order to solve the above problems, according to an aspect of the invention, there is provided a surface stress sensor including: a first flat member that includes a first fixed end and a first free end, the first free end being opposite to the first fixed end and being caused to be deflected by stress on a surface thereof; and a second flat member that is disposed on substantially the same plane as the first flat member and includes a second fixed end and a second free end, the second free end being opposite to the second fixed end, including a piezoresistive member in at least a part thereof and causing change in a resistance value of the piezoresistive member by deflection thereof. The first free end of the first flat member is connected to the second free end of the second flat member, and deflection of the first flat member applies a force to the second free end of the second flat member to cause the change in the resistance value of the piezoresistive member.

According to a second aspect of the invention, in the surface stress sensor according to the first aspect of the invention, the second flat member includes a fixed end side narrow portion and a flat member body, and the fixed end side narrow portion is disposed between the second fixed part and the flat member body and includes the piezoresistive member.

According to a third aspect of the invention, in the surface stress sensor according to the first or second aspect of the invention, the length between the first fixed end and the first free end of the first flat member is greater than the length between the second fixed end and the second free end of the second flat member.

According to a fourth aspect of the invention, in the surface stress sensor according to any one of the first to third aspects of the invention, substantially the entirety of the second flat member is the fixed end side narrow portion.

According to a fifth aspect of the invention, in the surface stress sensor according to any one of the first to fourth aspects of the invention, the first flat member and the second flat member are disposed in the same direction.

According to a sixth aspect of the invention, in the surface stress sensor according to any one of the first to fourth aspects of the invention, the first flat member and the second flat member are disposed to be opposite to each other.

According to a seventh aspect of the invention, there is provided a surface stress sensor including: a flat member in which stress is applied to a surface thereof, and which has at least one pair of fixed ends, the flat member including a flat member body and at least one fixed end side narrow portion, and the fixed end side narrow portion being disposed between the flat member body and one of the fixed ends. At least one fixed end side narrow portion includes a piezoresistive member, and deflection caused in the fixed end side narrow portion by the stress on the flat member causes change in a resistance value of the piezoresistive member.

According to an eighth aspect of the invention, there is provided a surface stress sensor including: a flat member in which stress is applied to a surface thereof, and which has at least two pairs of fixed ends. Each pair of fixed ends is disposed to be opposite to each other around the flat member, the flat member includes a flat member body and at least one fixed end side narrow portion, and the fixed end side narrow portion is disposed between the flat member body and one of the fixed ends. The at least one fixed end side narrow portion includes a piezoresistive member, and deflection caused in the fixed end side narrow portion by the stress on the flat member causes change in a resistance value of the piezoresistive member.

According to a ninth aspect of the invention, in the surface stress sensor according to the eighth aspect of the invention, the flat member includes two pair of fixed ends and four fixed end side narrow portions, the four fixed end side narrow portions are respectively related to the fixed ends, and each of the fixed end side narrow portions includes the piezoresistive member. Each of the fixed ends is connected to the flat member body through the related narrow portion among the fixed end side narrow portions. The piezoresistance coefficient of the piezoresistive member in the flat member is changed according to a direction in which the deflection is caused. Adjacent piezoresistive members among the piezoresistive members of the fixed end side narrow portions are connected to each other, the piezoresistive members forming a full bridge, and the piezoresistive members forming four sides of the full bridge.

According to a tenth aspect of the invention, in the surface stress sensor according to the ninth aspect of the invention, the flat member is a film of a p-type silicon single crystal, and a surface of the film is a (001) plane of the single crystal, and one of the pairs is disposed in a [110] direction of the single crystal, and the other pair is disposed in a [1-10] direction of the single crystal.

Effects of the Invention

The surface stress sensor according to the invention provides high sensitivity compared with the cantilever-based surface stress sensor in the related art, without using a structure that is complex and/or is difficult to manufacture. The surface stress sensor according to an exemplary embodiment of the invention is able to more stably detect surface stress compared with the related art by means of resistance against mechanical noise such as vibration around the sensor, movement of a liquid or the like, due to a structure without a free end.

BEST MODE FOR CARRYING OUT THE INVENTION

Figure 1:
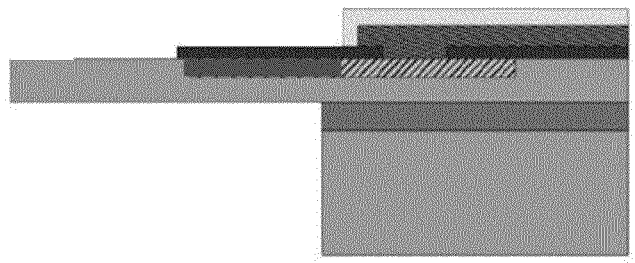
FIG. 1 is a diagram illustrating a main portion in a cross-sectional view of a cantilever of a piezoresistive cantilever array sensor.
Figure 2:
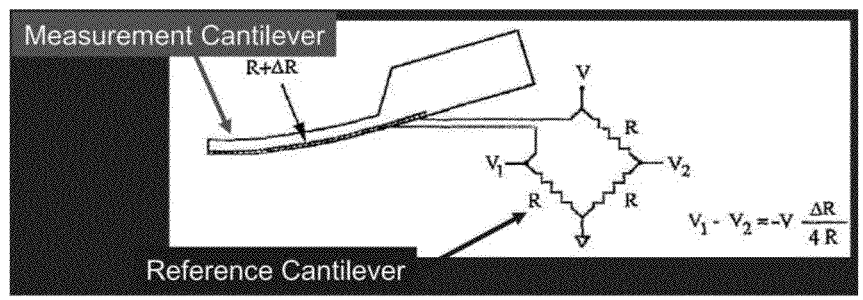
FIG. 2 is a circuit diagram schematically illustrating how to detect change in a piezoresistor provided on a surface of a cantilever.

In a surface stress sensor according to the invention, an "adsorption cantilever" and a "sensor cantilever" are provided, and both are combined at free ends thereof on the same plane. By using this geometry, with a configuration capable of being achieved in actual microfabrication, it is possible to concentrate the entire surface stress induced on the "adsorption cantilever" into a point force and to apply the point force to an end part of a piezoresistive "sensor cantilever".

In the surface stress sensor according to the embodiments of the invention, a new scaling rule with respect to a piezoresistive cantilever sensor is realized. That is, if an adsorption cantilever becomes large, sensitivity increases. By using a full bridge structure that employs an anisotropic high piezoresistance factor of single-crystal silicon, compared with a normal cantilever that employs a piezoresistive device having the same size, a rapid sensitivity increase of triple digits or greater is obtained according to the size of an adsorption lever or an adsorption film. Even in an actual design having a surface of 500×500 μm² on an adsorbing section, a high S/N, of more than 100 times compared with a piezoresistive cantilever designed for scanning is obtained. Since the present inventors already demonstrated (Non-Patent Document 10) the highest sensitivity (detection of a volatile organic compound at the level of sub ppm) using a cantilever designed for a scanning microscope, the new sensor, that is, the surface stress sensor (SSS) according to the invention is expected to provide high applicability in medical diagnosis, gene and environmental research, and all sensor applications in which high sensitivity is necessary for detection of a small amount of objects using a movable device at low cost.

Theoretical Background

A resistance value (R) of a piezoresistor and its relative resistance change ($\Delta R/R$) are given as follows.

[Expression 1]

$$R = \rho \frac{l}{wl} \quad (1)$$

$$\Delta R = \frac{\partial R}{\partial \rho}\Delta\rho + \frac{\partial R}{\partial l}\Delta l + \frac{\partial R}{\partial w}\Delta w + \frac{\partial R}{\partial t}\Delta t \quad (2)$$

$$\frac{\Delta R}{R} = \frac{\Delta \rho}{\rho} + \frac{\Delta l}{l} - \frac{\Delta w}{w} - \frac{\Delta t}{t} \quad (3)$$
$$= (\pi_x \sigma_x + \pi_y \sigma_y + \pi_z \sigma_z) + \varepsilon_x - \varepsilon_y - \varepsilon_z$$

Here, $\rho$, l, w and t represent resistivity, length, width and thickness of the piezoresistor, respectively, and $\sigma$ and $\varepsilon$ represent stress and strain induced in the piezoresistor. Further, $\pi$ represents a piezoresistance coefficient. Here, a subscript represents a direction, in which x, y and z correspond to a length direction, a transverse direction and a normal direction of a cantilever, respectively. The relationship between strain and stress can be deduced from the generalized Hooke's law.

[Expression 2]

$$\varepsilon_x = \frac{1}{E}[\sigma_x - v(\sigma_y + \sigma_z)] \quad (4)$$

$$\varepsilon_y = \frac{1}{E}[\sigma_y - v(\sigma_x + \sigma_z)]$$

$$\varepsilon_z = \frac{1}{E}[\sigma_z - v(\sigma_x + \sigma_y)]$$

Here, E and $v$ are the Young's modulus and the Poisson's ratio of the cantilever, respectively. Accordingly, if it is assumed that the stress is a planar stress (that is, $\sigma_z=0$), the relative resistance change can be expressed as follows.

[Expression 3]

$$\frac{\Delta R}{R} = \sigma_x\left(\frac{1+2v}{E} + \pi_x\right) + \sigma_y\left(-\frac{1}{E} + \pi_y\right) \quad (5)$$

Here, in order to acquire a large signal and to make the best use of a high piezoresistance coefficient of silicon, a cantilever that is formed by single-crystal Si (001) and has a p-type piezoresistor is considered. The piezoresistance coefficient is determined by the following relationship (Non-Patent Documents 17 to 19).

[Expression 4]

$$\pi_x = \tfrac{1}{2}(\pi_{11}+\pi_{12}+\pi_{44})$$

$$\pi_y = \tfrac{1}{2}(\pi_{11}+\pi_{12}-\pi_{44}) \quad (6)$$

Here, $\pi_{11}$, $\pi_{12}$ and $\pi_{44}$ represent crystalline basic piezoresistance coefficient. In the case of the p-type Si (001) in which the x direction and the y direction are arranged as [110] and [1-10], respectively, $\pi_{11}$, $\pi_{12}$ and $\pi_{44}$ are +6.6, −1.1 and +138.1, respectively, using $10^{-1}$ Pa$^{-1}$ as a unit. Accordingly, piezoresistance coefficients $\pi_x$ and $\pi_y$ are calculated as 71.8×$10^{-11}$ Pa$^{-1}$ and −66.3×$10^{-11}$ Pa$^{-1}$, respectively. Further, E and $v$ are 1.70×$10^{11}$ Pa and 0.28. Since $\pi_x \gg (1+2v)/E$, $\pi_y \gg -1/E$ and $\pi_x \cong -\pi_y \cong \pi_{44}/2$, Formula (5) can be approximated as follows.

[Expression 5]

$$\frac{\Delta R}{R} \approx \frac{1}{2}\pi_{41}(\sigma_x - \sigma_y) \quad (7)$$

Accordingly, a piezoresistive signal (that is, $\Delta R/R$) is mainly determined by a difference between $\sigma_x$ and $\sigma_y$.

Finite Element Analysis

Using finite element (FE) analysis or finite element analysis (FEA) based on COMSOL Multiphysics 3.5a, structures of a cantilever and an SSS are evaluated and optimized. The respective structures are divided into meshes of 5000 to 30000 elements, which provide a sufficient resolution in the present geometry.

A three-dimensional "pressure (unit N/m$^3$)" that is isotropically applied to a receptor film having a finite thickness can be expressed by two-dimensional "surface stress (unit N/m) on the basis of the following formula.

"surface stress (N/m)"="pressure (N/m$^2$)"×"film thickness (m)"

That is, a force having the unit of N/m can be considered as a force obtained by adding up the three-dimensional pressure in a film thickness direction. Here, in a case where the film thickness of the receptor film is very small, the receptor film may be approximately considered to be two-dimensional (surface). For example, in a case where a pressure of 10 MPa is applied to a receptor film of 10 nm, it can be considered that a surface stress of 10×10$^6$[Pa]×10×10$^{-9}$ [m]=0.1[N/m] is applied. That is, since the surface stress (s) relates to the surface, the surface stress (s) is assumed as the two-dimensional amount and is thus defined by N/m. However, in any actual case in which an in-plane stress is applied, the "surface" is not strictly two-dimensional, and expands to several atomic layers. Thus, the surface has a finite thickness ($t_{surf}$), and thus, the surface stress "s" can be represented as a three-dimensional "bulk" stress $\sigma$ as follows (Non-Patent Document 15).

[Expression 6]

$$s = \sigma \cdot t_{surf} \quad (8)$$

In the FE analysis, a thin gold film having an initial stress is disposed on the surface of a cantilever, and surface stress induced by a sample is simulated. It should be noted that, although it is possible to use an arbitrary different material as a "surface stress generating layer", in a material that is excessively hard or excessively soft, in other words, a material having an excessively large Young's modulus or an excessively small Young's modulus, there is a large difference between its result and the analysis results. In all the embodiments according to the invention, a thickness (10 nm) of the gold film and an applied initial stress (1.0×10$^7$ Pa) cause a surface stress of 0.1 N/m, which is generally determined to be a typical reported value of surface stress induced by a sample, such as adsorption of protein. Validity of the simulated surface stress is verified by comparing a value of a calculated displacement with an analytical solution based on Stoney's equation (Non-Patent Document 21) and the equation (Non-Patent Document 15) modified by Sader. Deviation from the analytic model is about 10% in Stoney's equation, and is about 1% in Sader's model, which shows a simulation with valid accuracy.

Result And Consideration a) Point Force and Uniform Stress

Figure 3:
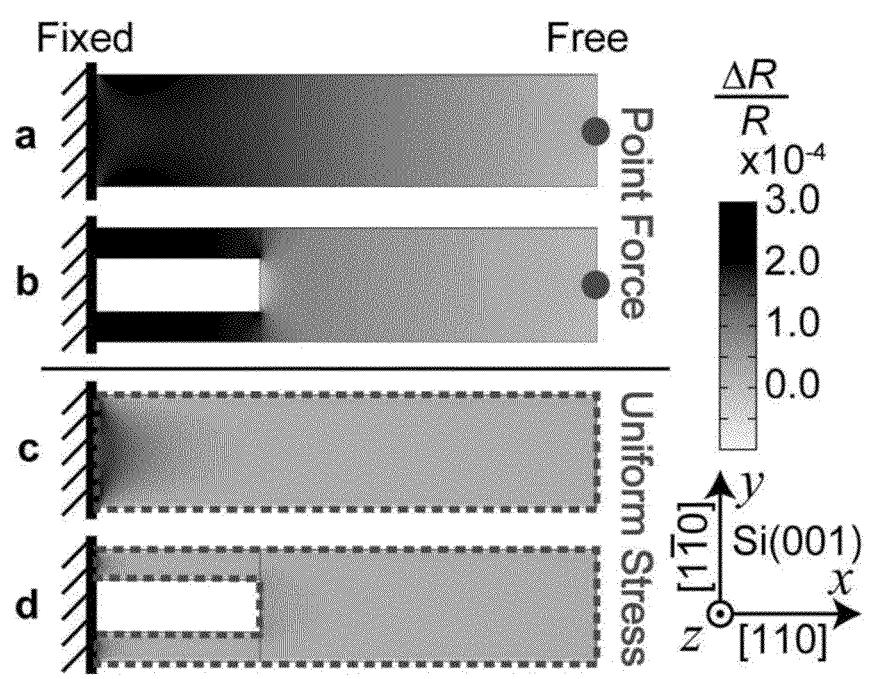
FIG. 3 is a diagram illustrating a calculation result of $\Delta R/R$ distribution on a surface of a cantilever of a case where a fixed end side narrow portion is present and a case where the fixed end side narrow portion is not present.

Stress distribution on the cantilever greatly depends on the type of an applied force. Since a piezoresistive signal, that is, $\Delta R/R$ is determined by $\sigma_x$ and $\sigma_y$, as understood from Formula (7), it is important to provide a piezoresistor at a location where larger stress that causes a larger difference between the x direction and the y direction is induced. FIG. 3 illustrates calculation results of $\Delta R/R$ distribution caused by a point force at a free end or uniformly dispersed stress, respectively. (a) and (b) show the case of a scanning probe microscope, and (c) and (d) show the case of a cantilever sensor. The length, width and thickness of a cantilever that are individually calculated are 135 µm, 30 µm and 1 µm, respectively, and two fixed end side narrow portions in (b) and (d) have a length of 45 µm, a width of 8 µm and a thickness of 1 µm. This is originally optimized for parallel scanning (Non-Patent Documents 21 and 22), and has the same shape as the piezoresistive cantilever of which high sensitivity (sensitivity of sub ppm for a volatile organic compound) and selectivity (identification of individual alkanes in a homologous series) are previously verified by the present inventors (Non-Patent Documents 10 and 21). As obviously understood from (a) and (b) of FIG. 3, stress is concentrated on a region close to the fixed end, and accordingly, in the case of the point farce (white circle), a higher $\Delta R/R$ is obtained in the region. Due to the fixed end side narrow portion at the fixed end, a signal effectively increases. It should be noted that a point force is applied so that displacements at the free ends in all the cases are the same (about 23 nm). Accordingly, by placing a piezoresistive part in the vicinity of the fixed end or in a portion on the fixed end side, the applied point force is effectively read by resistance change of the piezoresistor. In contrast, in the case of the cantilever sensor, stress induced by a sample is uniformly distributed on the entire surface of a cantilever, Due to an asymmetry effect at the fixed end, $\Delta R/R$ slightly increases in some regions, but noticeable stress concentration is not present even in the portion on the fixed end side, and thus, $\Delta R/R$ is relatively small. Further, even though the piezoresistive part is placed in any region, it is almost not possible to obtain a large signal. This is because $\Delta R/R$ is determined by the difference between $\sigma_x$ and $\sigma_y$, but as shown in (c) and (d) of FIG. 3, the stress is uniformly and isotropically applied onto the entire surface in most regions, that is, $(\sigma_x - \sigma_y) \cong 0$. In (c) and (d) of FIG. 3, in-plane stress (−0.1 N/m) is uniformly applied onto the entire surface.

b) Stress concentration due to double cantilever geometry

In order to solve the significant problem to enhance a piezoresistive cantilever performance for sensing use, the present inventors propose a new solution that a separate cantilever is introduced to concentrate surface stress that is uniformly distributed, in a specific region. That is, the separate cantilever having a piezoresistive part is referred to as a "sensor cantilever", with respect to the "adsorption cantilever". Free ends of the sensor cantilever and the adsorption cantilever are connected to each other on the same plane, and thus, the sensor cantilever and the adsorption cantilever can be simply manufactured.

Figure 4:
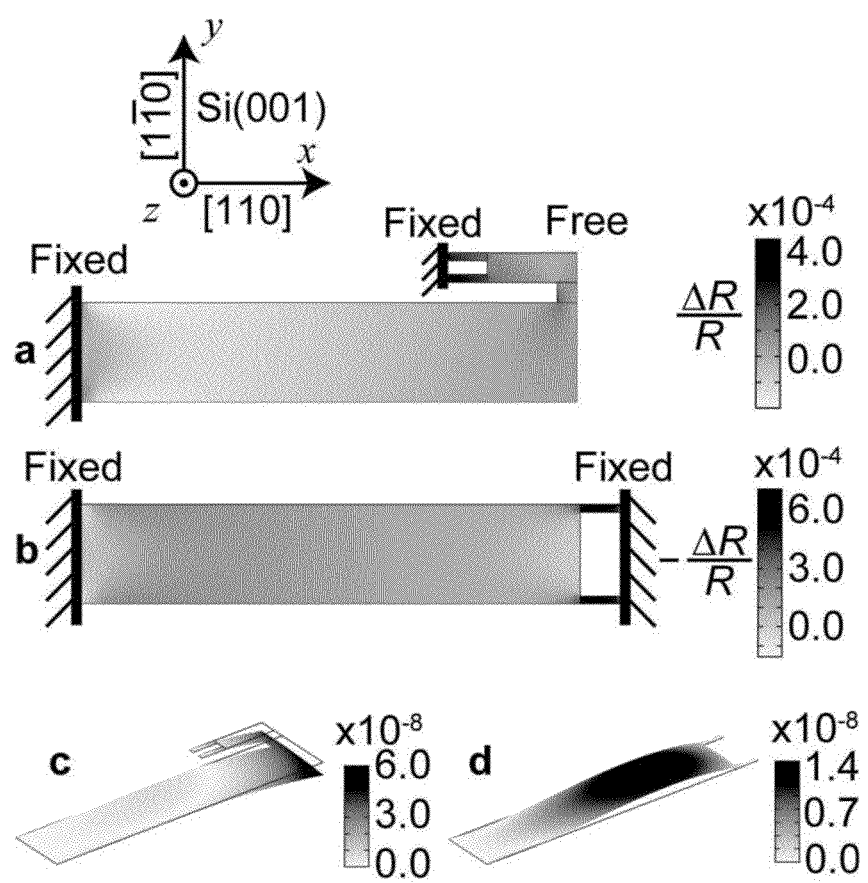
FIGS. 4(a) and 4(b) are diagrams illustrating $\Delta R/R$ distribution on a surface of a double cantilever configuration.
FIGS. 4(c) and 4(d) are diagrams illustrating shapes respectively deformed in FIGS. 4(a) and 4(b) when displacement of deformation is expressed in the unit of meters.

An example of the geometry is shown in (a) of FIG. 4. An upper small cantilever is a sensor cantilever ($135 \times 30 \times 1$ µm³; the same size as that in (d) of FIG. 3, and a lower large cantilever is an adsorption cantilever ($500 \times 100 \times 1$ µm³, an arbitrary geometry as an example). A basic solution of this design is two-fold. That is, 1) the entire surface stress that is uniformly distributed on the entire surface of the adsorption cantilever is accumulated at the free end in the form of displacement, and 2) the displacement shifts to the sensor cantilever as a point force applied to the free end of the sensor cantilever. Since the surface stress induced to the respective portions along the cantilever causes deflection of the corresponding portions of the cantilever, the deflection is accumulated at the free end. Accordingly, the displacement of the free end of the cantilever can be considered as the sum of the entire surface stress induced to the entire surface of the adsorption cantilever. The sensor cantilever receives the point force at the free end through the mechanical connection with the adsorption cantilever. This situation in the sensor cantilever is the same as the cantilever that operates for scanning for detection of the point force applied to the free end. As shown in (a) and (b) of FIG. 3), the point force applied to the free end induces stress concentrated in a region close to the fixed end, and here, the fixed end side narrow portion is able to effectively increase the stress. Accordingly, with the double cantilever geometry, it is possible to concentrate the entire stress induced on the surface of the adsorption cantilever in a region close to the fixed end of the sensor cantilever. The piezoresistive part buried in the stress concentrated region is able to effectively detect the entire surface stress applied to the adsorption cantilever. The stress concentration, and thus, larger $\Delta R/R$ can be seen in the fixed end side narrow portion in (a) of FIG. 4. The deformed shape of the double cantilever geometry is shown in (c) of FIG. 4. For quantitative comparison, an average value $(\Delta R/R|_{ave})$ of relative resistance change is calculated as follows.

[Expression 7]

$$\left.\frac{\Delta R}{R}\right|_{ave} = \frac{1}{A_R} \int_0^{A_R} \frac{\Delta R}{R} dA \qquad (9)$$

Here, $A_R$ is the area of the piezoresistive part. $\Delta R/R|_{ave}$ of the fixed end side narrow portion of the sensor cantilever in the double cantilever configuration ((a) of FIG. 4) is $2.85 \times 10^{-4}$, but this value in a normal cantilever ((d) of FIG. 3) is only $2.47 \times 10^{-5}$. Thus, according to the double cantilever, it is possible to obtain a signal of more than ten times the size using a sensor cantilever having the same size. However, in this geometry, in addition to stress that is not balanced due to an asymmetric shape, some force loss occurs in the connection portion. In order to solve this problem, the sensor cantilever may be directly connected to the adsorption cantilever along the transverse axis. It should be noted that stiffness of the sensor cantilever is minimized. This is because the stiffness causes reactions to the adsorption cantilever and has a negative influence on force transmission from the adsorption cantilever. According to analytic calculation, in a body portion (that is, a portion other than the fixed end side narrow portion) of the sensor cantilever, the value of $\Delta R/R$ increases on a wide side thereof, and the increase is approximately saturated at the same width as that of the adsorption cantilever. Further, if the width of the body portion of the sensor cantilever is larger than the width of the adsorption cantilever, loss in force transmission in the connection portion occurs. In consideration of this problem, the most efficient geometry is the geometry as shown in (b) of FIG. 4, that is, a structure in which the width of the sensor cantilever is the same as the width of the adsorption cantilever. This structure is a structure in which the fixed end side narrow portion of the sensor cantilever is directly connected to the adsorption cantilever. Thus, it is possible to suppress the loss of force to the minimum. Further, according to stress distribution balanced in the fixed end side narrow portion, the loss of the force from the adsorption cantilever is almost not present. It can be understood that the $\Delta R/R|_{ave}$ in the fixed end side narrow portion in (b) of FIG. 4 is $4.29\times10^{-4}$, but this is a value approximately 20 times larger than the normal cantilever in a case where the size of the piezoresistive member is the same. In the case of a double-clamped geometry ((d) of FIG. 4), for example, even though the same compressive stress (0.1 N/m) is applied to different geometries in FIGS. 3 and 4, it should be noted that the direction of displacement becomes opposite (upward) and the value of $\Delta R/R$ becomes negative.

c) Further Increase of Signal Using Full Bridge Geometry

Figure 5:
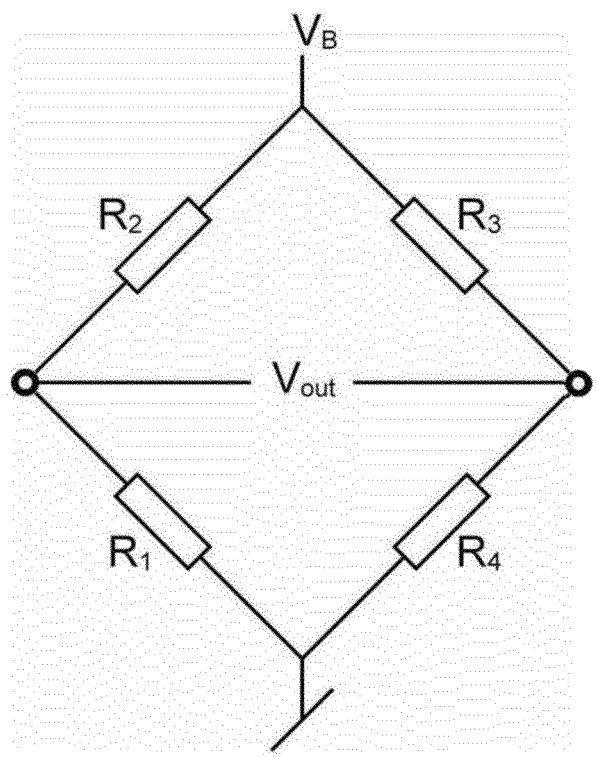
FIG. 5 is an equivalent circuit diagram illustrating a Wheatstone bridge configuration of a surface stress sensor of a full bridge configuration.

By using a characteristic of a silicon single crystal, it is possible to further enhance a signal. In many cases, $\Delta R/R$ is measured as a change in an output voltage ($V_{out}$) using a Wheatstone bridge as shown in FIG. 5.

[Expression 8]

$$V_{out} = \frac{V_B}{4}\frac{\Delta R}{R} \quad (10)$$

Here, $V_B$ is a bias voltage applied to the bridge. As normally applied to a pressure sensor, all four resistors ($R_1$, $R_2$, $R_3$ and $R_4$) in the Wheatstone bridge may be used as a part of the sensor. In this case, the total output can be determined as follows.

[Expression 9]

$$V_{out} = \frac{V_B}{4}\left(\frac{\Delta R_1}{R_1} - \frac{\Delta R_2}{R_2} + \frac{\Delta R_3}{R_3} - \frac{\Delta R_4}{R_4}\right) \quad (11)$$

Figure 6:
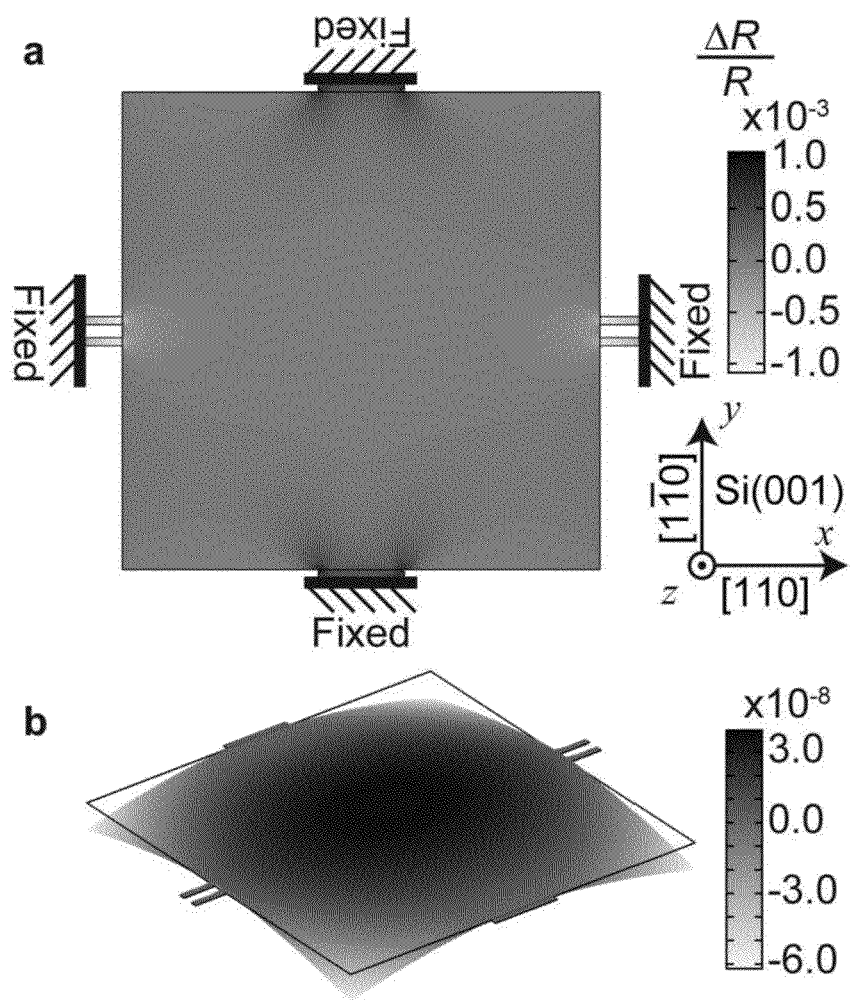
FIG. 6 is a diagram schematically illustrating a surface stress sensor of a full bridge configuration based on a p-type single crystal Si (001).
Figure 7:
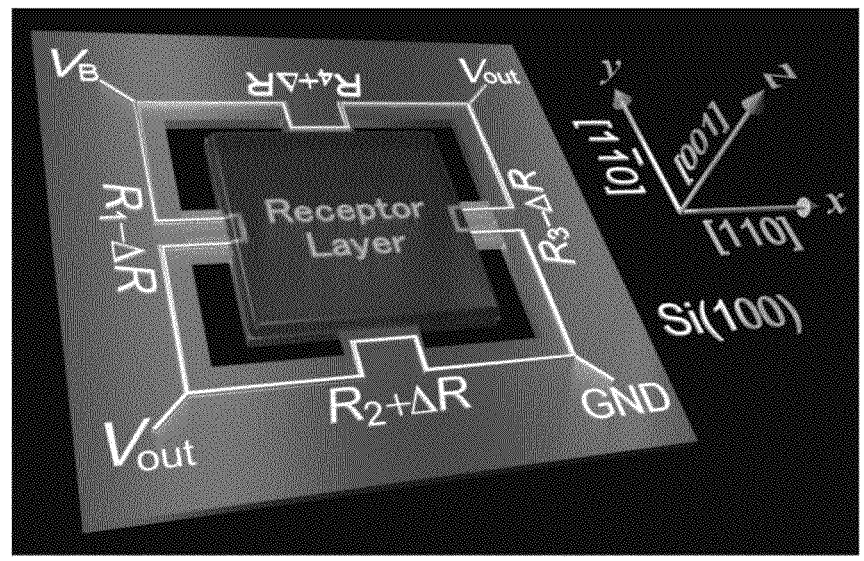
FIG. 7 is a perspective view illustrating the surface stress sensor of the full bridge configuration shown in FIG. 6.

This means that a $V_{out}$ signal that is four times larger by a combination of two sets of resistors in which resistance values are changed in opposite directions is obtained. As described in the paragraph directly above Formula (7), if an electric current flows in the direction [110] on the surface (001) of the p-type silicon single crystal, signs of piezoresistance coefficients in the direction [110] and the direction [1-10] are opposite to each other. By using this characteristic of the piezoresistance coefficient on the surface of the silicon single crystal, it is possible to realize the above-described basic advantage by the full bridge scheme as shown in FIGS. 6 and 7. Since the electric current flows along the x direction (that is, direction [110]) in all the resistors, the relative resistance change thereof is entirely given by Formula (7). A dominant stress is $\sigma_x$ in $R_1$ and $R_3$, and is $\sigma_y$ in $R_2$ and $R_4$. Thus, signs for the relative resistance change are opposite in each of the resistor sets. That is, in this configuration, since $\sigma_x$ and $\sigma_y$ are respectively dominant in the respective piezoresistors in the adjacent two piezoresistors (for example, $R_1$ vs $R_2$), ARM has opposite signs. This behavior is confirmed using the finite element analysis shown in FIG. 6. A square film having a side of 500 μm is supported by a fixed end side narrow portion of the same size as shown in FIGS. 3 and 6, that is, $45\times8\times1$ μm$^3$. It should be noted that $R_2$ and $R_4$ have the length of double (90 μm) that of $R_1$ and $R_2$, and have the same area (90×8 μm$^2$, $R_1$ and $R_3$ have the area of two 45×8 μm$^2$ areas connected in series) with respect to the electric current. The calculated values of these resistances are $\Delta R_1/R_1|_{ave}=\Delta R_3/R_3|_{ave}=-6.95\times10^{-4}$ and $\Delta R_2/R_2|_{ave}=\Delta R_4/R_4|_{ave}=4.395\times10^{-4}$. Accordingly, the total relative resistance change is calculated as $\Delta R_{total}/R_{total}|_{ave}=\Delta R_1/R_1|_{ave}-\Delta R_2/R_2|_{ave}+\Delta R_3/R_3|_{ave}-\Delta R_4/R_4|_{ave}=2.27\times10^{-3}$, which is a value that is approximately 100 times larger than a normal cantilever having a narrow piezoresistive part with the same size. The above-described configuration of the surface stress sensor is referred to as a membrane-type surface sensor (MSS) in the present specification. This is because the membrane is fixed at several places of a side in the vicinity of the membrane.

It should be noted that the full bridge configuration has additional advantages compared with the normal cantilever. Firstly, four resistors that form the Wheatstone bridge have almost the same physical characteristic such as temperature dependency of resistivity. This is because the resistors are manufactured by the same microfabrication process. Accordingly, since external noise such as thermal drift cancels out in a circuit, noise in a signal decreases. Secondly, a free end is not present in the full bridge configuration (full-clamped geometry). Accordingly, under the environment that a sample flows on a sensor array, during measurement using this geometry, especially, very high stability is achieved. Since one of the main problems of the cantilever sensor is insufficient stability due to a very flexible shape at the free end, the full bridge configuration or the double-clamped configuration achieves considerable improvement in stability, in addition to very high sensitivity.

It should be noted that the silicon membrane supported by the four fixed end side narrow portions is square in the present embodiment but may be a different shape. Specifically, since stress on a corner region of the square membrane mostly does not contribute to the change in resistance in the fixed end side narrow portion, the corner region may be removed. Actually, according to calculation in FEA, even with a circular film, there is a difference of several % at most compared with the output of the square membrane.

d) Size Dependency Toward Ultimate Sensitivity

Figure 8:
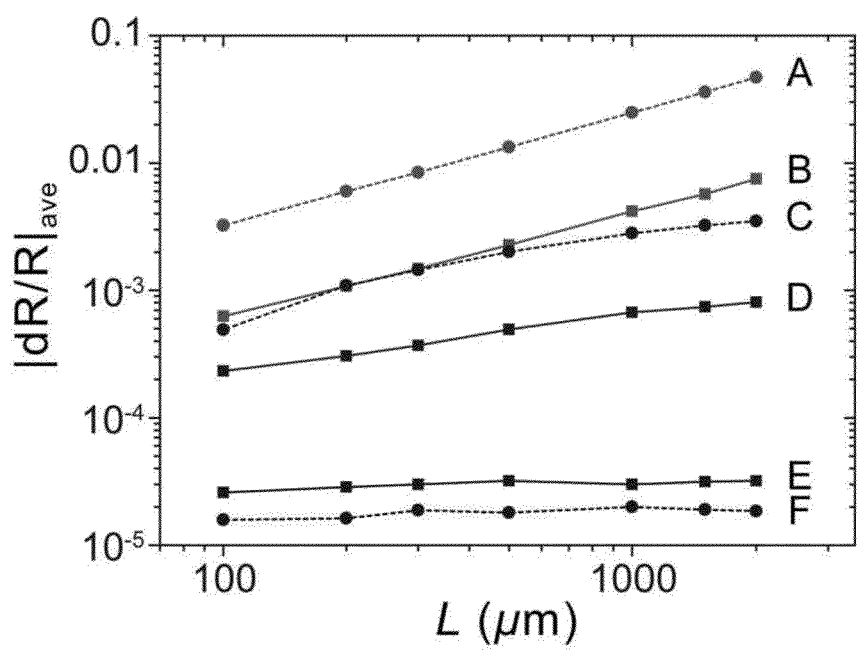
FIG. 8 is a graph illustrating dependency of an average relative resistance change ($\Delta R/R|_{ave}$) on the size (L) of an adsorption portion.

The most important difference between the normal cantilever and the double-clamped or full bridge geometry is size dependency of a signal. Since the entire induced stress can be concentrated on the piezoresistive part in the double-clamped or full bridge geometry, a new scaling rule "a larger adsorption cantilever causes higher sensitivity" is realized, which cannot be achieved in principle by any normal piezoresistive cantilever geometry. FIG. 8 illustrates size dependency with respect to relative resistance change in various geometries. Characteristics of the respective geometries are collected in Table 1. The scaling rule is obviously confirmed by the full bridge and double-clamped geometries, but |$\Delta R/R$| of an approximately constant level in the normal cantilever is given. It should be noted that, in a size range up to 2000 μm that is present herein, an amplification factor that exceeds three digits is achieved.

e) Signal-to-Noise Ratio

An actual performance of a sensor is determined by a signal-to-noise ratio (S/N). In the case of the piezoresistor, there are two main noises of Johnson noise ($V_j$) and Hooge (1/f) noise ($V_H$). These noises can be estimated by the following formula.

[Expression 10]

$$\overline{V_j^2} = 4k_B T \frac{l}{wt\mu q p}(f_{max} - f_{min}) \quad (12)$$

-continued $$\overline{V_H^2} = \frac{\alpha V_B^2}{hvtp} \ln\left(\frac{f_{max}}{f_{min}}\right) \quad (13)$$

Here, l, w and t represent the length, width and thickness of the piezoresistor, μ and ρ represent carrier mobility and carrier density, $k_B$, T and q represent the Boltzmann constant, temperature and electronic charge, $f_{max}$ and $f_{min}$ represent maximum measurement frequency and minimum measurement frequency, and α is the Hooge's constant. With respect to each geometry in the case of an actual size of L=500 μm, S/N estimated under a certain typical condition is collected in the following Table 1 (all parameter values under the typical condition are as follows: l=10 or 90 μm, w=2 or 8 μm, t=0.1 μm, μ=51 cm$^2$V$^{-1}$ s$^{-1}$, ρ=10$^{20}$ cm$^3$, $k_B$=1.38×10$^{-23}$ JK$^{-1}$, T=300 K, q=1.60×10$^{-19}$ C, $f_{max}$=5 Hz, $f_{min}$=1 Hz, α=10$^{-6}$, $V_B$=1.5 V).

TABLE 1

| | Config- uration | Area of piezoresistor | Width of adsorption portion | $|\Delta R/R|_{ave}$ in L = 500 μm | S/N in L = 500 μm |
|---|---|---|---|---|---|
| A | Full bridge[1] | 10 × 2 μm² | L (Square) | 1.3 × 10$^{-2}$ (591) | 16300 (107) |
| B | Full bridge[1] | 90 × 8 μm² | L (Square) | 2.3 × 10$^{-3}$ (105) | 15900 (105) |
| C | Double- clamped type[2] | 10 × 2 μm² | 100 μm | 2.0 × 10$^{-3}$ (91) | 2500 (16) |
| D | Double- clamped type[2] | 90 × 8 μm² | 100 μm | 4.9 × 10$^{-4}$ (22) | 3390 (22) |
| E | Normal cantilever[3] | 90 × 8 μm² | 100 μm | 2.2 × 10$^{-5}$ (1) | 152 (1) |
| F | Normal cantilever[3] | 10 × 2 μm² | 100 μm | 2.0 × 10$^{-5}$ (0.91) | 29 (0.19) |

[1] See FIG. 6 See (b) of FIG. 4 See (d) of FIG. 3

In the full bridge geometry, a high S/N value exceeding 100 times higher than the normal cantilever is estimated. The S/N value is a rough approximation, and in actual cases, it should be noted that it is necessary to consider various problems or trade-offs such as local current flow, heat consumption, carrier concentration, piezoresistance factor, carrier mobility and inverse proportional relation between other factors. In any case, since larger ΔR/R causes higher S/N all the time, the double-clamped or full bridge geometry has a simple configuration with respect to a sensing application based on surface stress, and provides a very high performance over the piezoresistive cantilever geometries.

Conclusion

A new geometry for optimization of the piezoresistive cantilever for a sensing application, based on surface stress concentration, is proposed. Using the double cantilever geometry that includes the double-clamped type and full bridge configuration, it is possible to concentrate the entire surface stress induced by the sample on the piezoresistive part. An effective concentration that causes sensitivity of several tens to several hundreds of times larger than the normal cantilever using the piezoresistive part having the same size, is verified by the finite element analysis. Due to this geometry, a new scaling rule that as the adsorption portion increases, the sensitivity increases is realized. Thus, only by changing the size of the adsorption portion, it is possible to design a surface stress sensor having arbitrary sensitivity suitable for each object of sensitivity that is several digits larger than that of the normal cantilever. This is simply referred to as the "surface stress sensor (SSS)" instead of the "cantilever" of the double-clamped or full bridge geometry.

EXAMPLES

Figure 9:
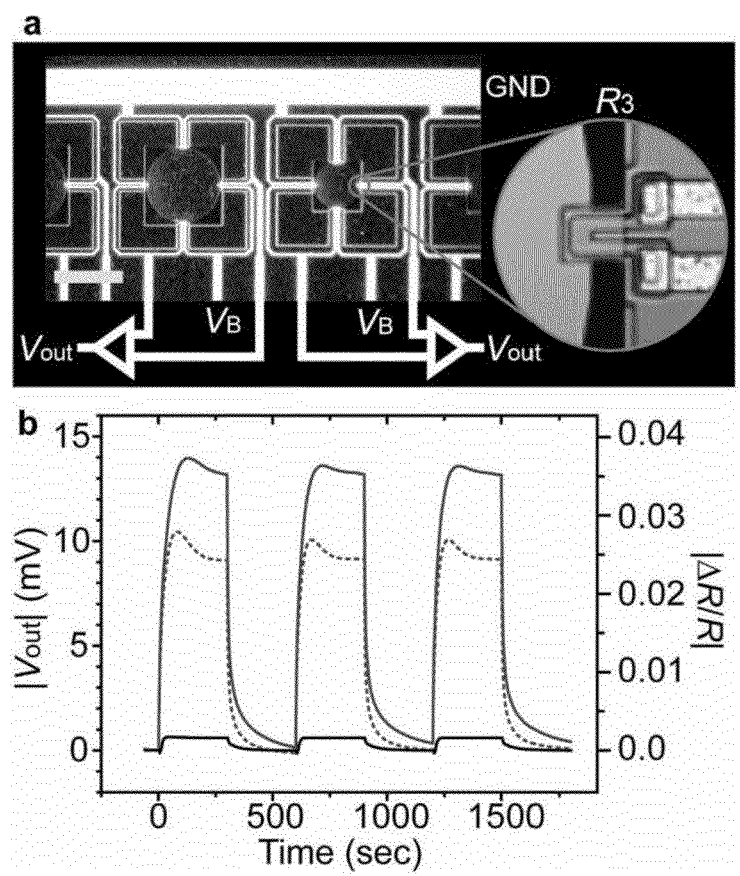
FIG. 9(a) is a diagram obtained by adding an electric connection circuit diagram to a photo of a manufactured membrane-type surface stress sensor (MSS) array chip, in which an inserted view illustrates an enlarged image of a piezoresistive detection beam part ($R_3$)
FIG. 9(b) is a graph illustrating a sensor output signal ($V_{out}$) from an MSS in the array.

In order to experimentally show the high sensitivity and size dependency, an MSS array shown in (a) of FIG. 9 is manufactured. A circular membrane is employed instead of a square membrane. According to a simulation, the circular membrane has slightly low (about 3%) sensitivity compared with the square shape, but has some actual advantages such that the flow of a sample is better due to a large opening around the membrane, through which a liquid sample can be simply coated using an ink jet and spotting method. In the same array as that in (a) of FIG. 9, two types of membranes having diameters of 500 μm and 300 μm are manufactured and are evaluated under the same conditions. For the purpose of comparison, a standard (reference) cantilever having the same size as shown in (d) of FIG. 3 is also tested. The lengths in the x direction and the y direction of MSS sensor beams are 10 μm and 16 μm with respect to $R_1$ and $R_3$, and 5 μm and 36 μm with respect to $R_2$ and $R_4$, in the configuration shown in FIGS. 6 and 7.

Figure 10:
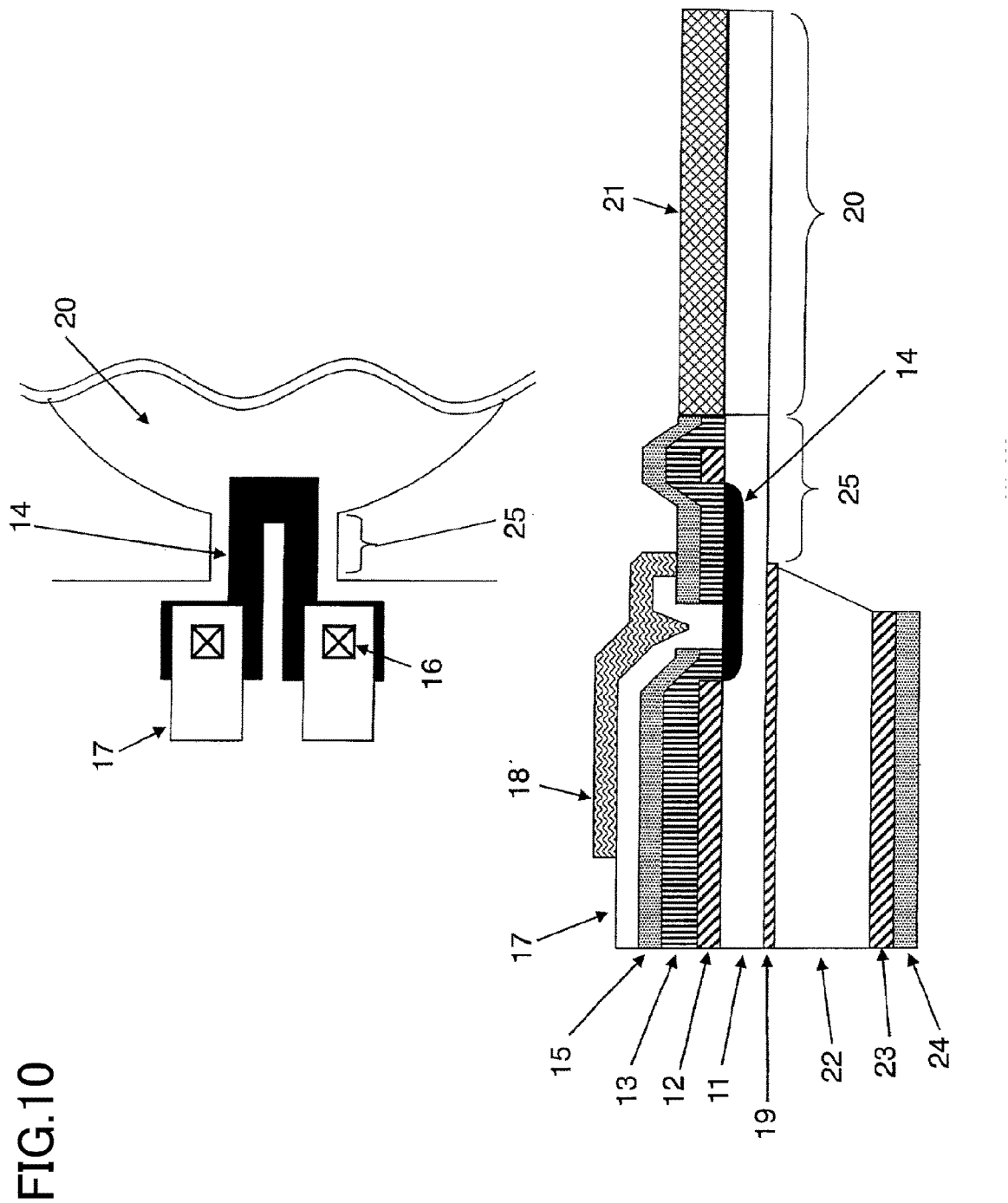
FIG. 10 is a cross-sectional view and a plan view of main parts of an example of a manufactured surface stress sensor.

These MSSs are manufactured as described below. Description will be made with reference to a cross-sectional view (lower view) and a plan view (upper view) in FIG. 10. A silicon-on-insulator (SOI) wafer of 4 inches, having an n-type device layer 11 (thickness of about 4 and about 10 Ωcm), is prepared. After the wafer is cleansed, an oxide film 12 of 700 nm is formed by thermal oxidation. Using etching in photolithography and buffered hydrogen fluoride (BHF), a piezoresistor shape is patterned in the oxide film 12. A double membrane 13 (thickness of 650 nm) having an oxide film that is not doped is accumulated on a boron-doped oxide film by chemical vapor deposition (CVD). Dispersion of boron is performed for 30 minutes at 950° C. In this process, boron is not dispersed to a wafer through the thermal oxide film 12, and is selectively dispersed only to a portion open to the piezoresistor shape, to thereby form a piezoresistive part 14. Using low pressure CVD, a silicon nitride film 15 is formed on the entire wafer surface. After the photolithography, a contact hole 16 is opened by plasma and BHF etching. In this step, an opening on a rear surface of the wafer for KOH etching is also formed. An aluminum film of 900 nm is deposited on the device side. Using a drawn photoresist mask, the aluminum film is etched with a chemical etching liquid to form a device electrode 17. In order to separate the electrode from the sample in a device operation, an oxide film 18 of a thickness of 700 nm is formed by plasma-enhanced CVD. Using photolithography and chemical etching, a pad opening is manufactured. Next, using photolithography and etching, a device layer of the wafer is processed to form a film. This wafer is mounted on a mechanical chuck and is dipped in KOH of 40 weight % at 60° C. to form a large opening from the rear surface. Etching is automatically stopped in a buried oxide film (BOX) 19. Finally, the BOX is etched in the BHF to form a membrane 20.

The membrane and the standard cantilever are coated with a polyethyleneimine (PEI) layer 21 using an inkjet spotting technique. An upper surface of the MSS (and the standard cantilever used for comparison with the MSS performed as described later) is coated by a customized inkjet spotting system (Microjet Model "LaboJet 500SP"). A PEI solution having a density of 1 g/l is deposited, to thereby form a PEI layer 21 of a thickness of 1 μm on the surface. It is confirmed that overflowing does not occur from the surface by real-time side surface monitoring during the deposition process.

Accordingly, as only the upper surface is coated with the PEI layer 21, it is possible to efficiently induce surface stress, but bilateral coating does not almost generate a signal due to competing forces from the both sides. In the figure, reference numeral 22 represents a bulk substrate, reference numeral 23 represents a thermal oxide film, reference numeral 24 represents a silicon nitride film, and reference numeral 25 represents a sensor cantilever.

These test pieces are exposed three times while performing purging using pure nitrogen for five minutes with a flow rate of 100 ml/minute at an interval of five minutes, in a state where water vapor of 20% is included in a pure nitrogen carrier gas. The entire system is set in a thermostat chamber that is maintained at 293.00±0.05K. The pure nitrogen gas is introduced into a sample bottle filled with pure vapor through a mass flow controller (Fujikin FCST1005C-4F2-F1L-N2), to send the mixed sample gas to a measurement chamber at a rate of 100 ml/minute in all. Before starting measurement, a state where the pure nitrogen gas flows for 10 minutes at the minimum is maintained, to thereby obtain a state where purging of impurity molecules from the PEI layer or thermal drift of the piezoresistor is saturated.

(b) of FIG. 9 shows output signals acquired by the MSS and the standard cantilever. Both the signals are measured by the same electrical setting where a bias voltage of −1.5 V is applied in both the cases. A low signal in the figure represents data on the standard cantilever, a high signal indicated by a solid line represents data on the MSS having a diameter of 500 μm, and a high signal indicated by a dashed line represents data on the MSS having a diameter of 300 μm. The membranes of the diameters of 500 μm and 300 μm represent signals of about 22 times and 15 times higher than that of the standard cantilever, respectively. Through the test result, considerably increased sensitivity and membrane size dependency can be obviously confirmed. The acquired signals are smaller to some extent than values (that are respectively about 46 times and 31 times with respect to membranes having manufactured sizes of 500 μm and 300 μm) calculated by the finite element method, which is considered to be caused by some parameters ignored by calculation, such as a surface profile caused by a dopant diffusion depth and an etching process. Although the thickness (3.2 μm) of the membrane and beam of the MSS is slightly greater than the thickness (1 to 1.5 μm) of the standard cantilever, considerably increased sensitivity is obtained. If the thickness decreases, stiffness of the membrane decreases, according to the finite element method, in order to cause a linear sensitivity increase, it is possible to further increase the amplification degree of sensitivity by three times in the MSS having the same thickness (1 to 1.5 μm) as the standard cantilever.

Addition

In order to further support the invention from the theoretical viewpoint, as an addition for the above-described description of the invention, there is provided a general scheme for presenting an algebraic model of a framework of mechanical strain amplification for piezoresistive strain detection of cantilever displacement and obtaining an optimal geometry under a given condition, particularly, under the condition that manufacturing is restricted. This model is verified by the finite element analysis. With respect to scanning based on a force applied to the free end of the cantilever, the fixed end side narrow portion at the fixed end functions well as a strain amplifier. In the case of detection of stress induced by adsorption, strain amplification is realized by the "double lever" geometry that includes two cantilevers of the sensor cantilever and the adsorption cantilever combined at both the free ends. In this geometry, surface stress on the adsorption cantilever induced by a sample is changed to surface strain at the fixed end of the sensor cantilever that receives a force.

A) Introduction

Detection of cantilever displacement is an important factor of many scanning applications and sensing applications using a cantilever. In the initial atomic force microscope (AFM) (Non-Patent Document 23), displacement is measured by a tunneling current. Immediately thereafter, various optical detection methods are used (Non-Patent Documents 24 to 28). Since noise is small, optical detection is attractive. On the other hand, it is necessary to perform adjustments such as light reflection alignment on a cantilever in which displacement detection of individual cantilevers in integrated cantilever arrangement is difficult and time-consuming, whenever a chip is exchanged. However, these two processes, that is, the displacement detection of the integrated cantilever and the chip exchange without light alignment are necessary in measurement of an opaque liquid such as blood, that is frequently necessary in various types of nanosystems in which a "large space" is not available, for example, in cantilever array (particularly, two-dimensional array), remote sensing and biological applications.

One of the most promising solutions for integrated detection is piezoresistive detection of cantilever displacement introduced by Tortonese and Quate (Non-Patent Document 27). This technique can simply minimize any size of cantilever, and also perform measurement in an opaque liquid such as blood, without using bulky peripheral devices as in optical reading. On the other hand, other exclusive integrated detection methods such as thermal detection (Non-Patent Document 29) used by Millipede have been successfully applied.

The piezoresistive detection has a characteristic that integration that is very important in application is possible, but is not yet widely used. The reason is as follows, for example:

a) The signal-to-noise ratio is lower than that of optical detection.

b) This method is more important in actual application and manufacturing since mass production is possible.

In order to improve the signal-to-noise ratio, various mechanical amplification methods of piezoresistive strain detection have been proposed as follows, for example:

a) A fixed end side narrow portion of a cantilever that is suitable for the case of a lever to which a point force is applied.

b) A double lever system that is suitable for the case of a cantilever to which stress is applied. The latter example corresponds to detection of strain caused by a bimorph type lever for detection of surface stress or temperature change as it is covered by an adsorbate.

Hereinafter, an algebraic expression for the strain amplification is given, and a scheme capable of simply and rapidly performing design of various mechanical amplification methods in a range of a normal manufacturing restriction and a necessary lever feature is considered. Various simplification assumptions are performed in which only a rectangular lever part is examined and a design guideline that is not changed very much is supported by the finite element analysis (FEA). It is possible to obtain strain amplification up to 40 times with respect to the micromachining process capable of performing mass production in the related art, and the amplification may increase the piezoresistive detection up to sensitivity of a level that is the same as or higher than that of the general optical method.

B) Basic Formula

Strain of a rectangular cantilever bent at a distance t from a neutral line is given by a curvature radius R as follows.

[Expression 11]

$$\varepsilon(x, \xi) = \frac{\xi}{R(x)} \quad (14)$$

Here, x represents a coordinate along an axis of a lever, and is x=0 at a fixed end. The strain causes the following bending moment $M_B(x)$.

[Expression 12]

$$M_B(x) = \int\int E(x)\varepsilon(x,\xi)\xi d\xi dw \\ = \frac{E(x)}{R(x)}\int\int \xi^2 d\xi dw \\ = \frac{E(x)I(x)}{R(x)} \quad (15)$$

Here, E(x) represents the Young's modulus. In a given position x, $I=[w(x)t(x)^3]/12$ represents an inertial area moment, and w(x) and t(x) represent width and thickness, respectively. It is assumed that E(x) is uniform on a given cross-section. $M_B$ is equal to a "load" moment $M_L$ operated on the lever in an equilibrium state. The following relationship is obtained in a small amount of bending.

[Expression 13]

$$\frac{1}{R} \sim \frac{d^2 z(x)}{dx^2} = M_L(x)H(x) \quad (16)$$

Here, $H(x)=1/[E(x)I(x)]$. A displacement z(x) of the lever in the z direction (direction perpendicular to the surface of the lever) at a position x is obtained by satisfying an appropriate boundary condition to integrate Formula (16). The surface strain of the lever at the position x is obtained by substituting the surface position ($\xi=t(x)/2$) for Formula (14) using Formula (16).

[Expression 14]

$$\varepsilon\left(x, \frac{t(x)}{2}\right) = \frac{t(x)}{2} M_L(x)H(x) \quad (17)$$

C) Lever To Which Force Is Loaded

1) Case Where Fixed End Side Narrow Portion Is Not Present (Simple Lever)

Here, assuming that w(x), t(x) and E(x), and accordingly, $H(x)=12/\{w(x)t(x)E(x)\}$ are all constants, a simple lever is firstly discussed. A force F at the free end of the lever causes a load moment $M_L(x)=F(l-x)$, and accordingly, the strain is largest at the fixed end (x=0). By substituting this formula relating to $M_L(x)$ in Formula (16), and by satisfying a boundary condition $dz(x)/dx|_{x=0}$ and z(0)=0 to continuously integrate Formula (16), a well-known formula for displacement is obtained.

[Expression 15]

$$z(x)=F(\tfrac{1}{2}lx^2-\tfrac{1}{6}x^3)H \quad (18)$$

The strain at the fixed end can be expressed by Formula (17) as follows.

[Expression 16]

$$\varepsilon_F = \frac{t}{2}M_L(0)H = \frac{t}{2}(Fl)H \quad (19)$$

This represents the "strain induced by the given force". However, in many cases (for example, in a force microscopy), a strain $\varepsilon_z$ induced by a given displacement at the free end attracts interest. In order to obtain a formula for $\varepsilon_z$, a force F in Formula (19) is removed using a displacement $z(l)=(\tfrac{1}{3})Fl^3H$ at the free end (x=l) from Formula (18), to obtain the following formula.

[Expression 17]

$$\varepsilon_z = \frac{3}{2}\frac{tz}{l^2} \quad (20)$$

(2) Case Where Fixed End Side Narrow Portion Is Present

Strain is proportional to H(x) using Formula (17), and its value is equal to $12/\{E(x)w(x)t^3(x)\}$. Accordingly, a large value of H is obtained by small values of width (w), thickness (t) and Young's modulus (E). In the surface stress sensor according to the invention, a configuration is used in which the width of a portion on the fixed end side that is a portion in the vicinity of an individual end of the sensor cantilever is locally reduced, and thus, a large value of H is caused. In the above-described example, the width (w) is set to a small value, but even though the thickness (t) decreases, the value of H can be set to be large. By forming the fixed end side narrow portion on the fixed end side, the most efficient function is achieved to obtain large strain. This is because $M_L$ is the largest at the position.

In the lever having the fixed end side narrow portion, displacement at the free end is obtained by satisfying a boundary condition that slope and displacement in a connecting portion from the fixed end side narrow portion to a perfect lever are continuous and by integrating Formula (16) at two stages, that is, from 0 to $l_C$ (length of the free end: side narrow portion; FIG. 11(b)) at the slope and the first stage, and from $l_C$ to l (length of the lever body portion; FIG. 11(b)) at the second stage. A formula for displacement at the free end z obtained as a result, lever stiffness S, strain $\varepsilon_{FC}$ at a given force, and strain $\varepsilon_{ZC}$ at a given displacement z is as follows.

[Expression 18]

$$z = \frac{1}{3}HFl^3\left\{1 + 3\left(\frac{1}{\alpha}-1\right)\left(\lambda-\lambda^2+\frac{1}{3}\lambda^3\right)\right\} = \frac{1}{3}HFl^3(1+\zeta) \quad (21)$$

$$S = \frac{F}{z} = \frac{3}{Hl^3(1+\zeta)} \quad (22)$$

$$\varepsilon_{F_c} = \frac{t_c}{2}M_L(0)H_c = \frac{t_c}{2}(Fl)H_c \quad (23)$$

-continued $$\varepsilon_{z_c} = \frac{3}{2} \frac{t_c z}{\alpha(1+\zeta)l^2} \quad (24)$$

Here, $\zeta=3[\{(1/\alpha)-1\}\{\lambda-\lambda^2+(\frac{1}{3})\lambda^3\}]$. $\alpha=H/H_C$ and $\lambda=l_C/l$. Coefficient $(1+\zeta)$ is considered as decrease in lever stiffness S due to the fixed end side narrow portion according to Formula (22). Here, further, force F in Formula (23) is removed using Formula (21). Since a case where both of $\alpha$ and $\lambda\ll1$ is discussed, $\zeta\cong3\lambda/\alpha$ may be approximated, and accordingly. $(1+\zeta)\cong(1+3\lambda/\alpha)$ and $\alpha(1+\zeta)\cong\alpha+3\lambda$ may be approximated in the following discussion. Strain amplifications $v_F$ and $v_{z,l}$ due to the fixed end side narrow portion at the given force F and the given displacement z from Formulas (19) and (23) and Formulas (20) and (24) can be expressed as follows.

[Expression 19]

$$v_F = \frac{\varepsilon_{Fc}}{\varepsilon_F} = \frac{t_c}{t} \frac{H_c}{H} = \tau \frac{w}{w_c} \frac{E}{E_c} \frac{t^3}{t_c^3} = \frac{\tau}{\beta\eta\tau^3} = \frac{\tau}{\alpha} \quad (25)$$

$$v_{z,l} = \frac{\varepsilon_{zc}}{\varepsilon_z} = \frac{\tau}{\alpha} \frac{1}{(1+\zeta)} = \frac{\tau}{\alpha+3\lambda} = \frac{\tau}{\beta\eta\tau^3+3\lambda} \quad (26)$$

Figure 12:
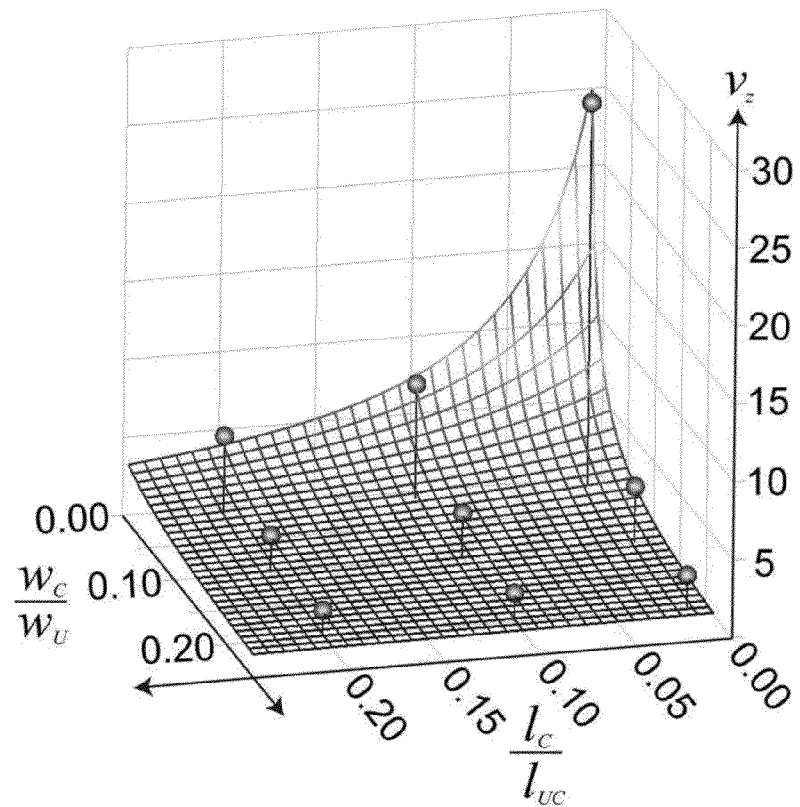
FIG. 12 is a diagram illustrating strain amplification due to a fixed end side narrow portion for a given displacement in the case of a point force.
Figure 13:
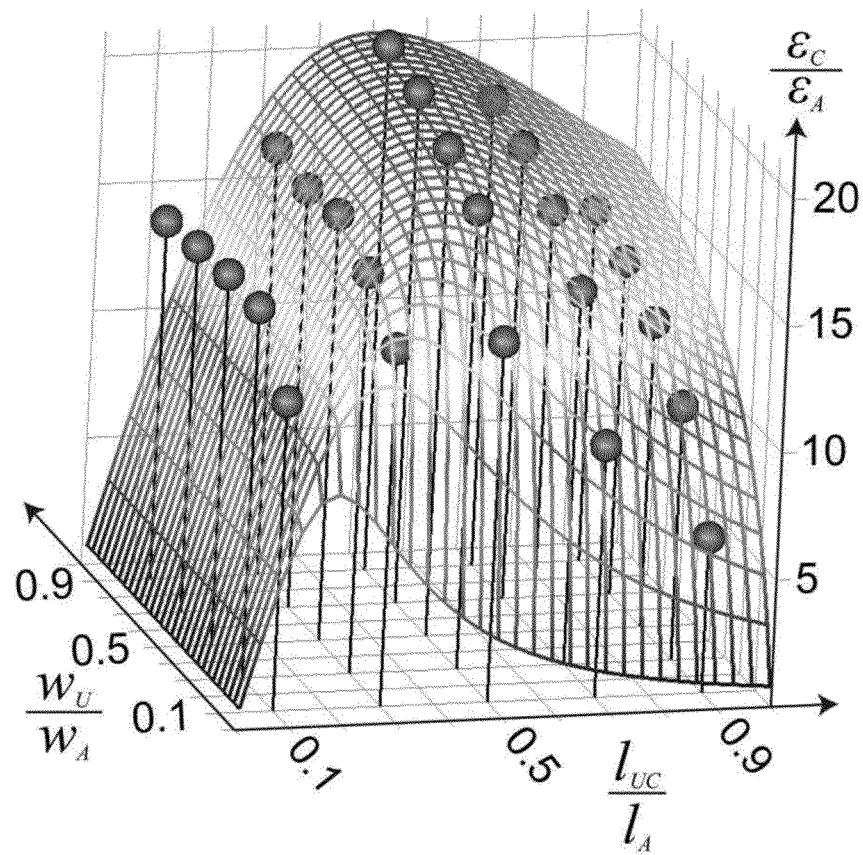
FIG. 13 is a diagram illustrating strain amplification for a given surface stress applied to a surface of an adsorption cantilever in the case of double lever geometry.

Here, $w_c$, $t_c$ and $E_c$ represent parameters of the fixed end side narrow portion, and $\beta=w_c/w$, $\tau=t_c/t$, $\eta=E_c/E$, and $\alpha=\beta\eta\tau^3$. As understood from Formula (25), strain is amplified by $\tau/\alpha$ times for the given force, but strain amplification for the given displacement decreases by lever stiffness factor $(1+\zeta)$ times. $v_{z,l}(\alpha, \lambda)$ does not have a maximum value for a given $\tau$. $v_{z,l}$ is monotonically changed from $v_{z,l}\tau/\alpha$ for $3\lambda\ll\alpha$ to $v_{z,l}=\tau/(3\lambda)$ for $3\lambda\gg\alpha$. In other words, if only one of $\alpha$ and $\lambda$ is very small, the strain amplification mainly depends on the other parameter, and as a result, a fixed end side narrow portion that is inefficient for strain amplification is achieved. Accordingly, both of $\alpha$ and $\lambda$ are set to be small, as obviously observed with reference to FIG. 12, it is important to set $\alpha$ to be the same level as $3\lambda$. FIG. 12 is a diagram illustrating strain amplification by means of a fixed end side narrow portion for a given displacement in the case of a point force. Dependency on the ratio of the length of the fixed end side narrow portion and the ratio of the width thereof ($l_C/l_{UC}$ and $w_c/w_u$) is shown. The value obtained by Formula (10) in the addition is shown as a shaded wireframe in the range of $0.01\leq l_c/l_{uc}\leq0.25$ and $0.01\leq w_c/w_u\leq0.25$, and on the other hand, the result calculated by FEA is shown as gray balls. On the other hand, $v_{z,l}(\tau)=\tau/(\beta\eta\tau^3+3\lambda)$ is maximized with respect to given $\beta$, $\eta$ and $\lambda$ as follows.

[Expression 20]

$$\tau_{Max} = \left(\frac{3\lambda}{2\beta\eta}\right)^{1/3} \quad (27)$$

This is determined by Formula (21).

$\partial v_{z,l}(\tau)/\partial\tau=0$ [Expression 21]

Amplification degree is determined by $\tau_{Max}$ as follows.

[Expression 22]

$$v_{z,l,\tau} = \frac{2^{2/3}}{3^{5/3}\lambda^{2/3}(\beta\eta)^{1/3}} = \left(\frac{4}{3^5\lambda^2\beta\eta}\right)^{1/3} \quad (28)$$

In the case of $2\beta<3\lambda$, it is necessary that $\tau<1$ with respect to the thickness in order to obtain a high amplification degree.

An independent fixed end side narrow portion, that is, $\beta=\eta=1$ causes a maximum amplification degree $v_{z,l,\tau}=(2^2/3^5)^{1/3}/\lambda^{2/3}\cong7.7$ with respect to $\lambda=0.006$. (The following is used as an exemplary lever: S=1 N/m, t=2 μm, w=80 μm and l=320 μm. In this case, $w_c=l_c=2$ μm, $\alpha=0.025$ ($\eta=\tau=1$) and $\lambda=0.006$.) Combined with the width of the fixed end side narrow portion, there are some gains in amplification degree with respect to the given $\beta$ and $\lambda$. However, this is relatively modest. This is because stiffness decreases by $v_{z,l,\tau}\propto1/(1+\zeta)$ $\propto\alpha$, and the amplification degree $v_{z,l,\tau}$ also decreases. In a case where the parameters of the fixed end side narrow portion are $\beta\eta=0.025$ in $\lambda=0.006$, $v_{z,l,\tau}=26(\tau_{Max}=0.71)$ is obtained compared with $v_{z,l}=23(\tau=1)$.

So far, amplification degree $\mu_{z,l}$ by means of the fixed end side narrow portion at the given displacement and lever length is handled, but there is interest in the calculation of the maximum strain for each parameter of the entire lever and the fixed end side narrow portion, instead of the amplification degree $\mu_{z,l}$. The strain at the given displacement increases as the length of the lever decreases (Formula (24)), but decreases as stiffness decreases ($\varepsilon_{zc}=t_czHlS/2\alpha$, Formulas (22) and (24)). Accordingly, if loss of stiffness is balanced by shortening the lever, it is possible to considerably increase the strain. Local parameters for entirely maximizing the strain are parameters $w_c$, $t_c$, $E_c$ and $l_c$ in the fixed end side narrow portion, and parameters $\alpha$, $\beta$, $\eta$, $\tau$ and $\lambda$ in the reduced fixed end side narrow portion, given by the manufacturing process. Further, the stiffness and band width or the lever response time is determined according to application methods. Firstly, sizes w, t, l and E of the lever that do not include the fixed end side narrow portion are selected, and then, the conditions of stiffness and band width are satisfied. In order to obtain a favorable amplification degree, $3\lambda$ should be the same as $\alpha=\beta\eta\tau^3$, and t should have a space for making the fixed end side narrow portion thinner. The selected lever is a favorable example as a start point. By making the fixed end side narrow portion short, wide or thick, it is possible to compensate for tenderization due to the fixed end side narrow portion. Hereinafter, a case where the lever is reduced is selected. This is because this selection is more efficient compared with a case where the width of the lever increases. Further, an option in which the amplification degree is maximized with respect to the thickness of the fixed end side narrow portion may be secured.

Firstly, a fixed end side narrow portion in which $\alpha=\beta\eta$, that is, $\tau=1$ is considered. If the size of a lever in which the fixed end side portion is not narrow is expressed by a subscript u, it is possible to obtain the following result with respect to stiffness $S_u=F/z$ in Formula (22) (here, since $\lambda=0$ with respect to the lever in which the fixed end side portion is not narrow, $\zeta=0$.).

[Expression 23]

$$S_u = \frac{E_u w_u t_u^3}{4l_u^3} = \frac{Y}{4l_u^3} \quad (29)$$

$S_u$ is set to be equal to the stiffness of the reduced lever, and $l_1 = ul_u$ and $S_1 = Y/[4l_1^3(1+3\lambda_1/\beta\eta)] = Y/[4l_1^3(1+3\lambda/_u\beta\eta)]$ (it should be noted that $\alpha = \beta\eta$ is not changed due to lever shortening, but $\lambda$ becomes $\lambda_1 = \lambda/u$), to obtain the following formula. Here, u is a shortening factor, and $Y = w_A/w$.

[Expression 24]

$$u^3\left(1 + \frac{3\lambda}{u\beta\eta}\right) = 1 \quad (30)$$

Since it is assumed that the shortening factor u is close to 1, by substituting the shortening factor u in Formula (30) as $1-\delta$ and by performing calculation in consideration of the terms up to $\delta^2$, a value of $\delta$ is obtained, and the following formula is obtained by substituting the value of $\delta$ for $1-\delta$.

[Expression 25]

$$u = 1 - \frac{\lambda}{\beta\eta + \lambda} \quad (31)$$

Further, the following formula is obtained with respect to the amplification degree.

[Expression 26]

$$v_{z,S} = \frac{1}{u^2\left(\beta\eta + \frac{3\lambda}{u}\right)} \quad (32)$$

It is possible to further increase the amplification degree by $\tau_{Max} = (3\lambda_2/2\beta\eta)^{1/3}$ by making the fixed end side narrow portion thinner (see Formula (27)). Here, as $I_2 = u_\tau l_0$, $\lambda_2 = \lambda/u_\tau$ and $\alpha = \beta\eta\tau_{Max}^3 = 3\lambda_2/2$, and $S_u$ is set to be equal to $S_2 = Y/[4l_2^3(1+3\lambda_2/\alpha)] = Y/[4l_2^3(1+2)]$ (it should be noted that $\tau_{Max}$, accordingly, $\alpha$ is given by the actual length of the elongated fixed end portion of the reduced lever $\lambda_2 = \lambda/u_\tau$), $u_\tau^3 = 1/3$ is obtained for the shortening factor, and the amplification degree is obtained as follows.

[Expression 27]

$$v_{z,S,\tau} = \quad (33)$$

$$\frac{\varepsilon_{zc,S,\tau}}{\varepsilon_z} = \left(\frac{t_c}{t}\right)\frac{1}{(\beta\eta\tau_{Max}^3 + 3\lambda_2)u_\tau^2} = \frac{\tau_{Max}}{\left(\frac{9}{2}\frac{\lambda}{u_\tau}\right)u_\tau^2} = \left(\frac{4}{3^5\beta\eta\lambda^2 u_\tau^4}\right)^{1/3}$$

Increase in amplification degree as the stiffness S is maintained as a constant is moderate if $\tau = 1$, but may be relatively considerable in $\tau_{Max}$. The following formula is obtained from Formulas (26) and (32) (it should be noted that $\tau = 1$).

[Expression 28]

$$\frac{v_{z,S}}{v_{z,I}} = \frac{\beta\eta + 3\lambda}{u^2\left(\beta\eta + \frac{3\lambda}{u}\right)} \quad (34)$$

This value is about 1.44 with respect to the exemplary lever. The following formula is obtained from Formulas (15) and (20).

[Expression 29]

$$\frac{v_{z,S,\tau}}{v_{z,I,\tau}} = u_\tau^{-4/3} \quad (35)$$

This value is generally about 1.63. If S is maintained as a constant, the amplification degree increases from $v_{z,I} = 23$ to $\mu_{z,S} = 32$, and from $v_{z,I,\tau} = 26$ to $v_{z,S,\tau} = 42$, respectively.

At the given force and stiffness, the same scheme is applied to the amplification degree. Even though $\tau_{Max}$ is not present and the thickness of the fixed end side narrow portion is any thickness included in $\alpha = \beta\eta\tau^3$, the shortening factor u is obtained from Formula (29). The amplification degree decreases by u, which is given by the following formula.

[Expression 30]

$$v_{F,S} = \frac{\tau}{\alpha}u \quad (36)$$

D) Double Lever

Displacement $\epsilon_A$ of a "single" adsorption cantilever in which uniform stress is given on the surface is expressed as follows,

[Expression 31]

$$\epsilon_A = \frac{1}{2}t_A M H_A \quad (37)$$

Figure 11:
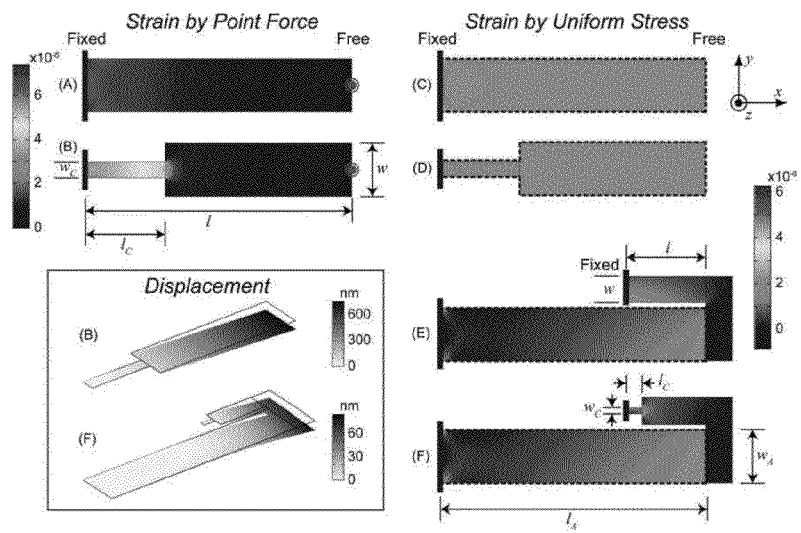
FIG. 11 is a diagram illustrating strain amplification in various geometries.

FIG. 11 illustrates strain amplification in various geometries. The x-directional strain is expressed by shading. A point force (10 nN) is applied to a point indicated by an edge which is present at the right end of each cantilever in (A) and (B). In (C) and (D), anisotropic surface stress (0.1 N/m) is induced to the surface of the entire cantilever, but in the cantilevers of (E) and (F), anisotropic surface stress is induced to the surface of the adsorption lever that is a region surrounded by a broken line. In (B) and (F), strain is effectively increased in the fixed end side narrow portion. The shapes of (B) and (F) deformed by the applied point force or the surface stress are shown in inserted figures. Values used in this figure are as follows (in the unit of μm). With respect to (A) to (D), $l_{uc} = 500$, $l_c = 150$, $w_u = 100$, and $w_c = 30$. With respect to (E) and (F), $w_A = 100$, $l_{uc} = 150$, $l_c = 30$, $w_u = 50$, and $w_c = 10$. Further, in all the cases, the thickness is 1 and the Young's modulus is 170 GPa.

Further, FIG. 12 shows strain amplification in the case of double layer geometry with respect to given surface stress applied to the surface of an adsorption lever. Dependency on the ratio of the lengths of the adsorption lever and the sensor lever and the ratio of the widths thereof ($l_{uc}/l_A$ and $w_u/w_A$) is shown. The value obtained by Formula (17) in the addition is shown as a shaded wireframe, and the result calculated by FEA is shown as gray balls. If a value of the ratio relating to the width increases, the amplification degree considerably increases, but the maximum value is present at a position of $l_{uc}/l_A$ of a certain value with respect to arbitrarily given $w_u/w_A$.

Since the bending moment induced by uniform stress is a constant, in contrast to strain (Formula (1), FIGS. 11(A) and (B)) with respect to the point force, $\epsilon_A$ does not depend on an actual position, as shown in FIGS. 11(C) and (D). In order to amplify the strain with respect to the uniform stress, a double lever geometry (FIGS. 11(E) and 11(F)) in which two cantilevers of the sensor cantilever and the adsorption cantilever are provided and are connected at free ends thereof, is discussed. In the case of the double lever geometry, the connection with the sensor cantilever reduces displacement of the adsorption cantilever by an action-reaction force $F_R$, and thus, the following formula is obtained.

[Expression 32]

$$z_A = \tfrac{1}{2} M H_A l_A^2 - \tfrac{1}{3} F_R H_A l_A \tag{38}$$

Displacement (z) of the sensor cantilever in which a force is induced by the adsorption cantilever and a fixed end side narrow portion is provided may be expressed as Formula (21). Since end points of both of the adsorption cantilever and the sensor cantilever are strongly connected to each other, $z_A$ is equal to z. Accordingly, $F_R$ is removed from Formula (21) and Formula (38), to thereby obtain the following displacement.

[Expression 33]

$$z_A = z = \frac{M H_A l_A^2}{2\left(1 + \dfrac{H_A l_A^3}{H l^3 (1+\zeta)}\right)} \tag{39}$$

Strain $\epsilon_c$ at the fixed end of the sensor cantilever may be calculated according to Formula (19) as follows.

[Expression 34]

$$\varepsilon_C = \frac{3 M H_A t_C}{4\alpha} \frac{1}{(1+\zeta)\lambda_A^2 + \dfrac{\alpha_A}{\lambda_A}} \tag{40}$$

Finally, the amplification degree ($\epsilon_A = t_A M H_A/2$) compared with a "single" adsorption cantilever having the same size as that of the adsorption cantilever in the double lever geometry is obtained as follows.

[Expression 35]

$$\nu = \frac{\varepsilon_C}{\varepsilon_A} = \frac{3\tau_A \tau}{2\alpha} \frac{1}{(1+\zeta)\lambda_A^2 + \dfrac{\alpha_A}{\lambda_A}} \tag{41}$$

Thus, it is possible to calculate the strain amplification degree for a given geometry. However, in order to maximize the amplification degree, the combination of the respective parts, that is, the adsorption cantilever, the sensor cantilever and the fixed end side narrow portion should be optimized.

The following formula is obtained according to $d\nu/d\lambda_A = 0$.

[Expression 36]

$$\lambda_{A,Max} = \left(\frac{\alpha_A/2}{1+\zeta}\right)^{1/3} \tag{42}$$

By substituting the $\lambda_{A,\,Max}$ for $\lambda_A$ in Formula (41), the following formula is obtained.

[Expression 37]

$$\nu_{Max} = \frac{\tau_A \tau}{2\alpha}\left(\frac{\alpha_A}{2}\right)^{-2/3}(1+\zeta)^{-1/3} \tag{43}$$

TERMINOLOGY l, w, t and E represent the length, width, thickness and Young's modulus of a cantilever or a sensor lever in a double lever configuration.

$l_c$, $w_c$, $t_c$ and $E_c$ represent the same values as above in a fixed end side narrow portion of a lever. Here, it should be noted that $l_c$ is a part of l.

$l_A$, $w_A$, $t_A$ and $E_A$ represent the same values as above in a lever covered by a uniform surface stress load, that is, an adsorbate.

H, $H_c$, $H_A$ = $12/Ewt^3$, which is the same in subscripts C and A.

$\lambda$, $\lambda_A$ = $l_c/l$, $l/l_A$ $\beta$, $\eta$ and $\tau$ represent $w_c/w$, $E_c/E$ and $t_c/t$, respectively.

$\alpha$ and $\alpha_A$ represent $H/H_c \beta \eta \tau^3$ and $H_A/H_s$, respectively.

$\epsilon_F$ and $\epsilon_M$ represent x-directional surface stress in a given force, and load moment, respectively.

$\epsilon_z$ represents the same value as above in a given lever displacement z.

$\epsilon_{Fc}$, $\epsilon_{Mc}$ and $\epsilon_{zc}$ represent the same values as above in a fixed end side narrow portion.

$\nu_z$ and $\nu_A$ represent a strain amplification degree due to a fixed end side narrow portion and a strain amplification degree due to a double lever, respectively.

z(x) and z represent displacements of a lever at a position x, which are displacements at a free end and at a "connection" position between a sensor lever and an adsorption lever, respectively.

F represents a force applied to a free end of a cantilever or a "connection" position between a sensor lever and an adsorption lever.

$M_L$ represents a load moment due to a force or uniform surface stress.

X = $l_A/l$

Y = $w_A/w$

INDUSTRIAL APPLICABILITY

An optimized SSS which achieves several digits of sensitivity amplification compared with a normal cantilever due to various advantages in actual application, such as a small size, low cost, no need for laser alignment and usability in an opaque liquid will open the door to a new era of various applications such as medical diagnosis, genetic and environmental research and detection of a very small amount of target molecules. Further, in many cases, it is important to note that mechanical detection of surface stress induced by a structural change is a unique characteristic of a cantilever. Thus, the SSS provided herein makes an important contribution to an analysis of various phenomena in which observation of a structural change is essential for finding a principle, and establishes a "nano stress analysis" that is a new analysis method.

EXPLANATION OF REFERENCE NUMERALS

11 DEVICE LAYER
12 OXIDE FILM
13 DOUBLE MEMBRANE
14 PIEZORESISTIVE PART
15 SILICON NITRIDE FILM
16 CONTACT HOLE
17 DEVICE ELECTRODE
18 OXIDE FILM
19 BURIED OXIDE FILM (BOX)
20 MEMBRANE
21 POLYETHYLENEIMINE (PEI) LAYER
22 BULK SUBSTRATE
23 THERMAL OXIDE FILM
24 SILICON NITRIDE FILM
25 SENSOR BEAM

The invention claimed is:

1. A surface stress sensor comprising:
a first flat member that includes a first fixed end and a first free end, the first free end being opposite to the first fixed end and being caused to be deflected by surface stress applied to a surface thereof; and
a second flat member that is disposed on the substantially same plane as the first flat member and includes a second fixed end and a second free end, the second free end being opposite to the second fixed end, including a piezoresistive member in at the second fixed end side of the second flat member so that a change in a resistance value of the piezoresistive member is caused by deflection thereof,
wherein the first free end of the first flat member is directly, mechanically connected to the second free end of the second flat member so that deflection of the first flat member directly applies a force to the second free end of the second flat member to cause the change in the resistance value of the piezoresistive member.

2. The surface stress sensor according to claim 1, wherein the second flat member includes a fixed end side narrow portion and a flat member body, and the fixed end side narrow portion is disposed between the second fixed end and the flat member body and includes the piezoresistive member.

3. The surface stress sensor according to claim 1, wherein the length between the first fixed end and the first free end of the first flat member is greater than the length between the second fixed end and the second free end of the second flat member.

4. The surface stress sensor according to claim 1, wherein substantially the entirety of the second flat member is the fixed end side narrow portion.

5. The surface stress sensor according to claim 1, wherein the first flat member and the second flat member are disposed to be opposite to each other.

6. A surface stress sensor comprising:
a flat member in which surface stress to be sensed is applied to a surface thereof, and which has at least one pair of fixed ends, the flat member including a flat member body and at least one fixed end side narrow portion, the pair of fixed ends being disposed along a periphery of the flat member body and being located oppositely each other across the flat member body, and the at least one fixed end side narrow portion being disposed between the flat member body and one of the fixed ends,
wherein the at least one fixed end side narrow portion includes a piezoresistive member so that deflection caused in the fixed end side narrow portion by the surface stress on the flat member causes change in a resistance value of the piezoresistive member.

7. A surface stress sensor comprising:
a flat member in which surface stress is applied to a surface thereof, and which has at least two pairs of fixed ends,
wherein each pair of fixed ends is disposed to be opposite to each other around the flat member,
wherein the flat member includes a flat member body and at least one fixed end side narrow portion, and the fixed end side narrow portion is disposed between the flat member body and one of the fixed ends, and
wherein the at least one fixed end side narrow portion includes a piezoresistive member so that deflection caused in the fixed end side narrow portion by the surface stress on the flat member causes change in a resistance value of the piezoresistive member.

8. The surface stress sensor according to claim 7, wherein the flat member includes two pair of fixed ends and four fixed end side narrow portions, the four fixed end side narrow portions are respectively related to the fixed ends, and each of the fixed end side narrow portions includes the piezoresistive member,
wherein each of the fixed ends is connected to the flat member body through the related narrow portion among the fixed end side narrow portions,
wherein a piezoresistance coefficient of the piezoresistive member in the flat member is changed according to a direction in which the deflection is caused, and
wherein adjacent piezoresistive members among the piezoresistive members of the fixed end side narrow portions are connected to each other, the piezoresistive members forming a full Wheatstone bridge, and the piezoresistive members forming four sides of the full Wheatstone bridge.

9. The surface stress sensor according to claim 8, wherein the flat member is a film of a silicon single crystal, the piezoresistive member constituting a part of the flat member is a p-type, and a surface of the film is a (001) plane of the single crystal, and
wherein pair of the two pairs of the fixed ends is disposed in a [110] direction of the single crystal, and the another pair is disposed in a [1-10] direction of the single crystal.

10. The surface stress sensor according to claim 7, wherein the fixed end side narrow portion is disposed substantially in the same plane as the flat member body.

* * * * *